United States Patent [19]

Ueno et al.

[11] Patent Number: 5,100,879
[45] Date of Patent: Mar. 31, 1992

[54] METHOD OF TOPICALLY CLEANSING THE HUMAN BODY

[75] Inventors: Ryuzo Ueno; Ryuji Ueno, both of Nishinomiya; Sachiko Kuno, Hyogo; Akihiko Tabata, Nishinomiya, all of Japan

[73] Assignee: K.K. Ueno Seiyaku Oyo Kenkyujo, Osaka, Japan

[21] Appl. No.: 398,318

[22] Filed: Aug. 24, 1989

Related U.S. Application Data

[63] Continuation-in-part of Ser. No. 176,065, Mar. 31, 1988, abandoned.

[30] Foreign Application Priority Data

Mar. 31, 1987 [JP] Japan ................. 62-80119

[51] Int. Cl.$^5$ ............... A61K 31/715; A61K 31/735
[52] U.S. Cl. .................... 514/59; 514/54; 252/121; 252/550; 424/405
[58] Field of Search ............... 514/54, 56, 59, 55; 252/121, 550, 10, 105; 424/405

[56] References Cited

U.S. PATENT DOCUMENTS

| | | | |
|---|---|---|---|
| 4,374,832 | 2/1983 | Joseph et al. | 514/25 |
| 4,522,814 | 6/1985 | Nonomura et al. | 514/54 |
| 4,710,493 | 12/1987 | Landsberger | 514/56 |
| 4,734,403 | 3/1988 | Dussourd D'Hinterland et al. | 514/54 |

FOREIGN PATENT DOCUMENTS

| | | |
|---|---|---|
| B12625 | 3/1983 | Australia . |
| B12631 | 3/1983 | Australia . |
| 1146859 | 5/1983 | Canada . |
| 0066379 | 12/1982 | European Pat. Off. . |
| 0115888 | 8/1984 | European Pat. Off. . |
| 0232744 | 8/1987 | European Pat. Off. . |
| 0240098 | 10/1987 | European Pat. Off. . |
| 3601136 | 7/1987 | Fed. Rep. of Germany . |

OTHER PUBLICATIONS

Hallinan, et al. Cancer Biochemistry Biophysics, vol. 5, pp. 97–101 (1981), "Inhibition of Reverse Transcriptase by Polyvinyl Sulfate (PVS)".
Kashiwa et al; Chem. Ab. 84:76174g (1976).
Barford et al; Chem. Ab. 91:194988a (1979).
Contamin et al; Chem. Ab. 96:91491g (1982).
Pola Chem.; Chem. Ab. 99:10689q (1983).
Yanagioa; Chem. Ab. 106:38254f (2-9-1987).
Asahara et al; Chem. Ab. 106:55633w (2-23-1987).
Nakagawa; Chem. Ab. 107:157018n (11-2-87).
Arch. of Aids Res., vol. 1, No. 1, 1987, pp. 45–56.
J. Natl. Cancer Inst., vol. 67, No. 4, pp. 899–910 (1981).
J. Virol., vol. 2, pp. 886–893 (1976).
Annals New York Acad. Sci., vol. 130, 365–373 (1965).
DiCioccio et al, Cancer Research, 38, 2401–2407 (1978).
Ehlers et al, J. gen Virol (1984), 65, 423–428 and 1325–1330.
Deringer, Funkt. Biol. Med., 4, 129 (1985).
Walton, British Journal Pharmacology, 7, 370 (1952), 8, 340 (1953) and 9, 1 (1954).
Ricketts, Biochem., 51, 129 (1952).
Mitsuya et al. Proc. Natl. Acad. Sci. USA, 82, 7096–7100 (1985).
Mitsuya et al. Proc. Natl. Acad. Sci. USA, 83 1911–1915 (1986).
Fauci; Proc. Natl. Acad. Sci. USA 83:9278–9283 12/1986.
Solomon et al; J. Bacteriology 92(6):1855-6 (1966).
Kiehl et al; J. Nat. Cancer Inst. 51(5):1705-7 (1973).

(List continued on next page.)

*Primary Examiner*—Johnnie R. Brown
*Assistant Examiner*—Nancy S. Carson
*Attorney, Agent, or Firm*—Sughrue, Mion, Zinn, Macpeak & Seas

[57] ABSTRACT

A method of disinfection for retroviruses which comprises contacting inanimate object in need of such treatment with a natural or synthetic oligo- or polysaccharide having at least one S-oxoacid group attached to the saccharic carbon atom through a linking group of low molecular weight.

18 Claims, 14 Drawing Sheets

OTHER PUBLICATIONS

Schaffrath et al; Hoppe—Seyler's Z. Physiol. Chem. 357:499-508 (1976).
Ito et al; Antiviral Research 7:361-7 (1987).
Hirose et al; Biochem. Biophys. Res. Commun. 149(2):562-7 (1987).
Tochikura et al; Jpn J. Cancer Res. 78:583-9 (1987).
Nakashima et al; Antimicrob. Agents Chemother. 31(10):1524-8 (1987).
Sydow et al; Biomed. Biochim Acta 46(6):527-30 (1987).
Nagumo et al; Jpn. J. Cancer Res. 79:9-11 (1988).
Nakashima et al; Jpn. J. Cancer Res. 78:1164-8 (1987).

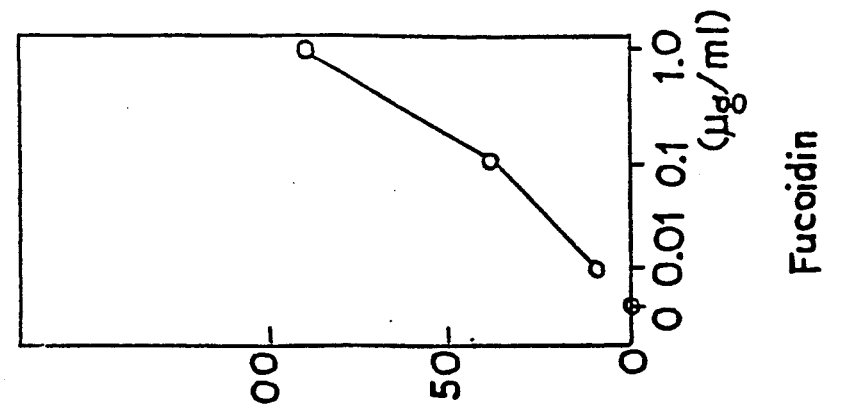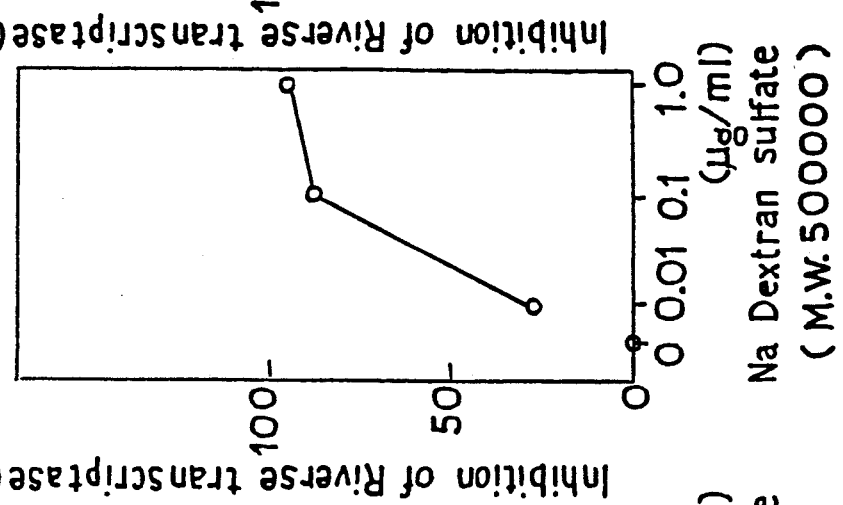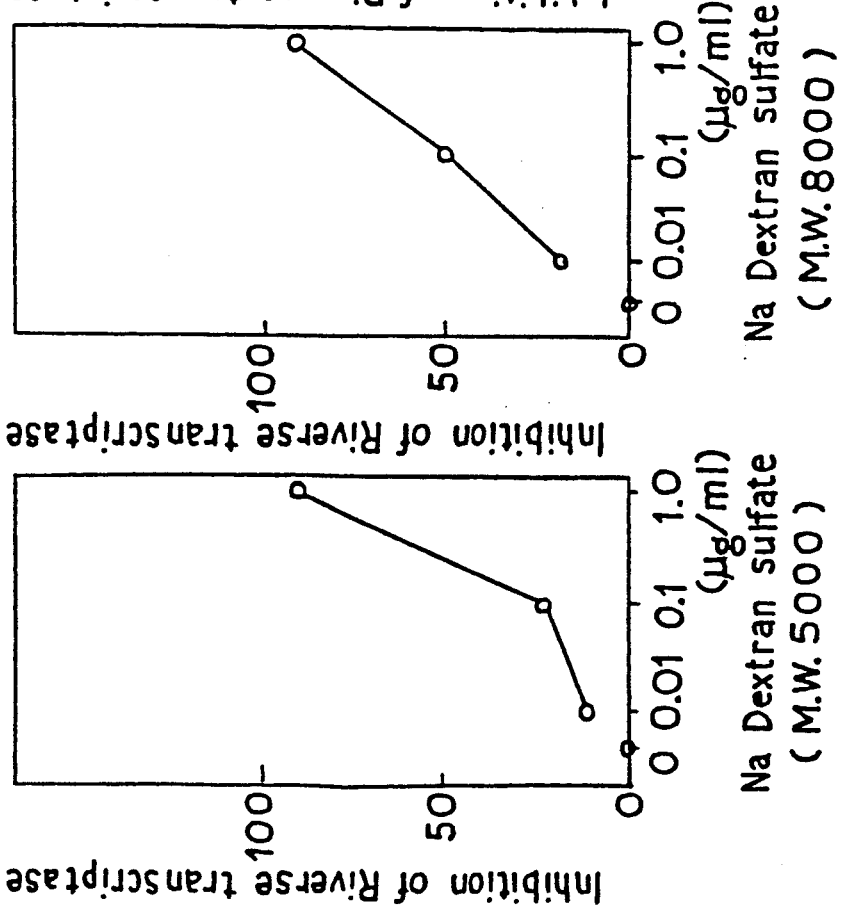

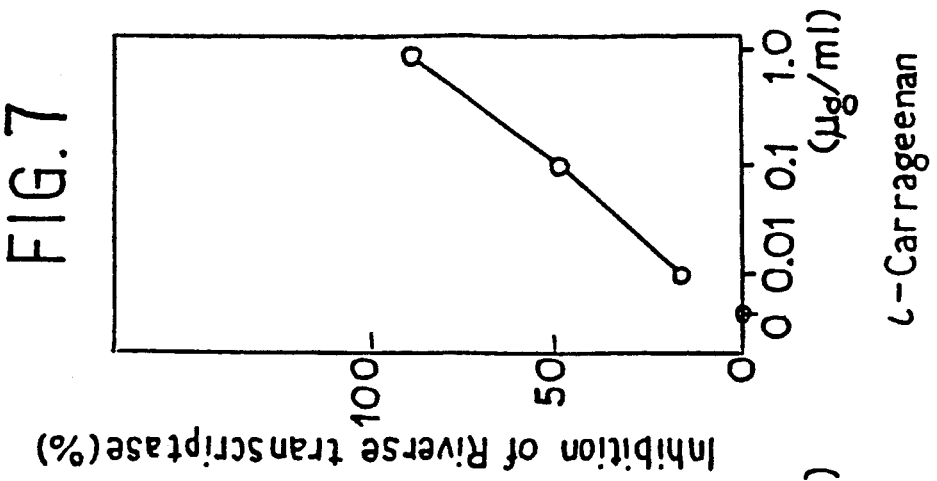
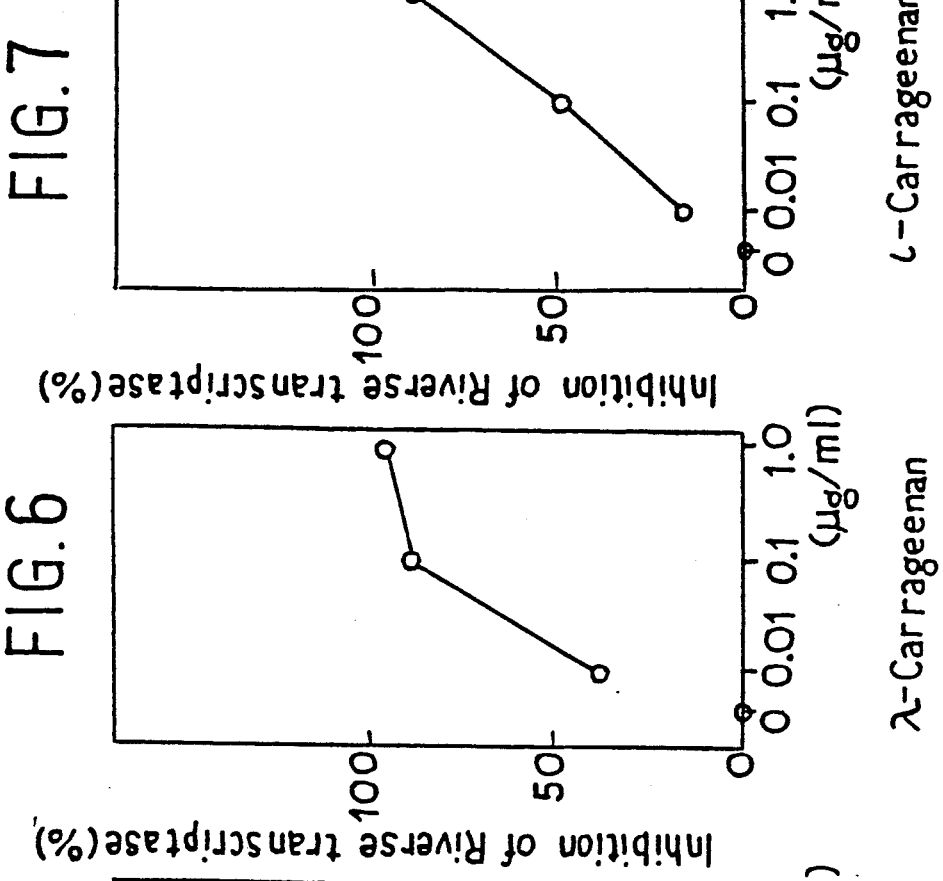
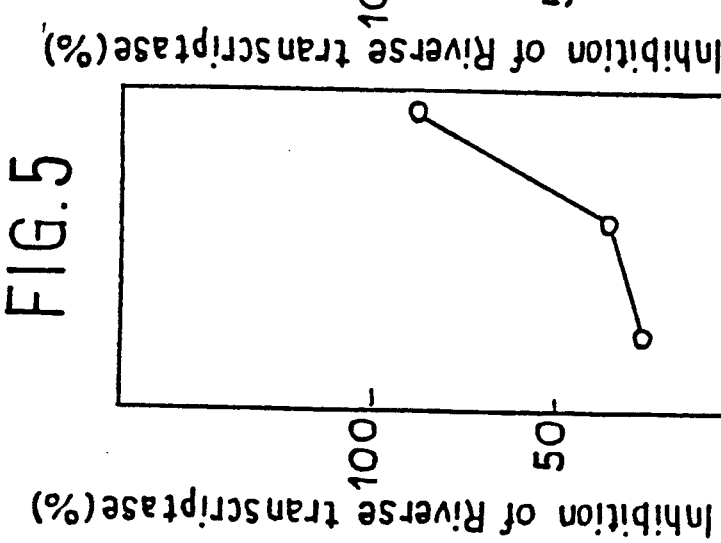

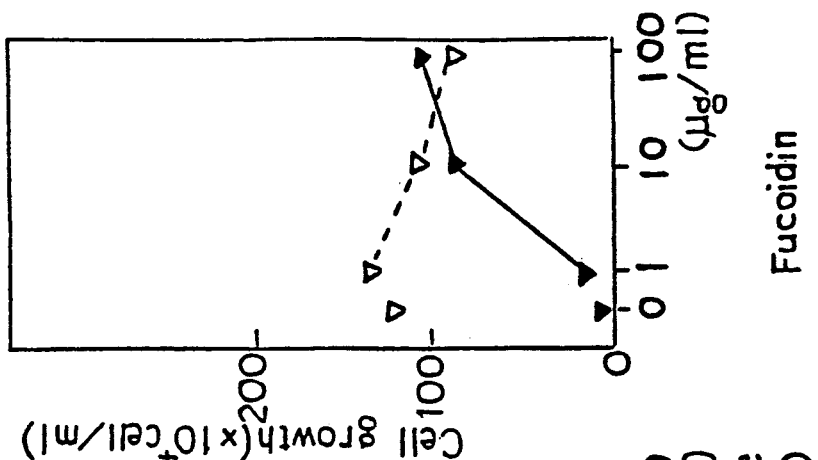
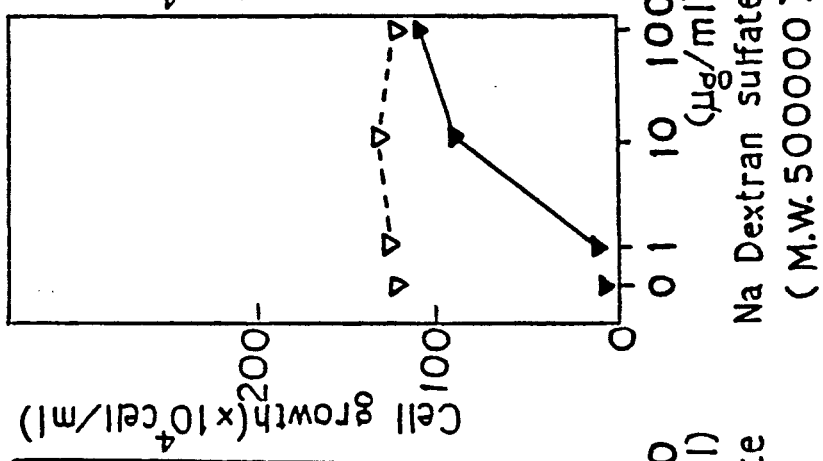
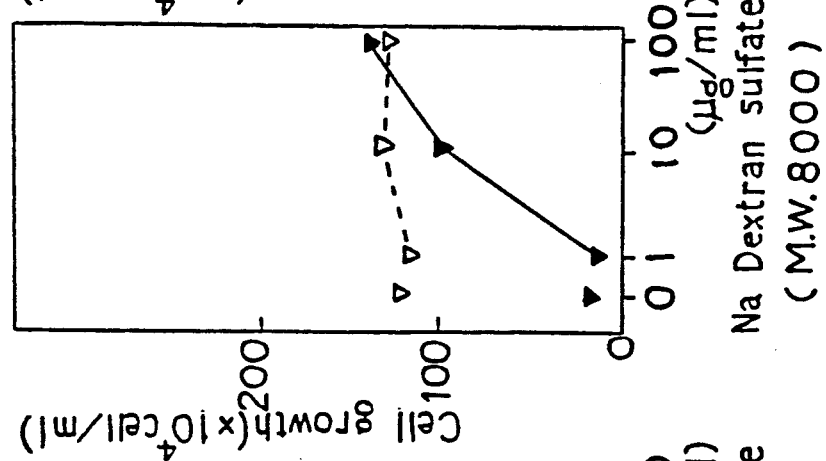
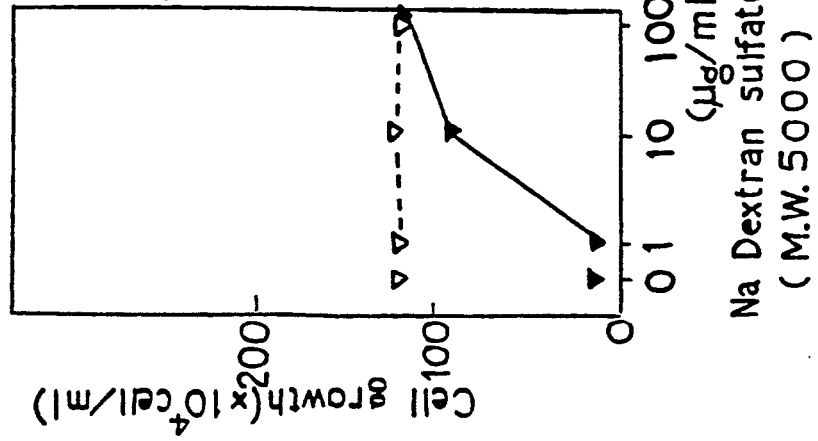

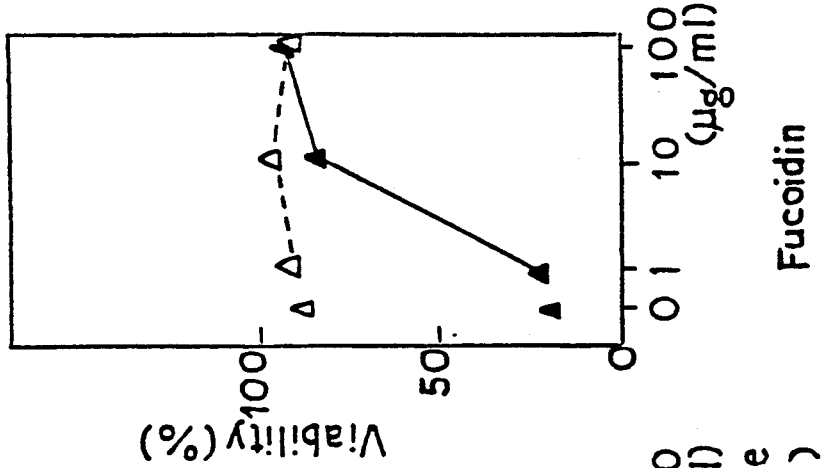
FIG. 19
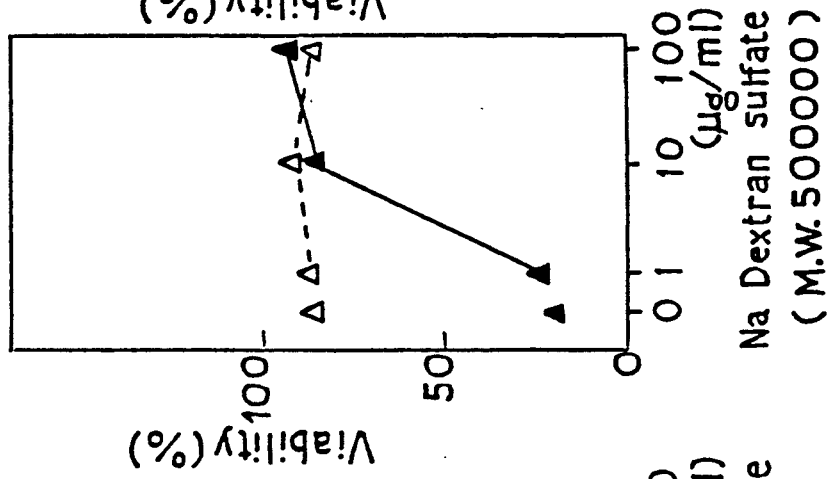
FIG. 18
FIG. 17
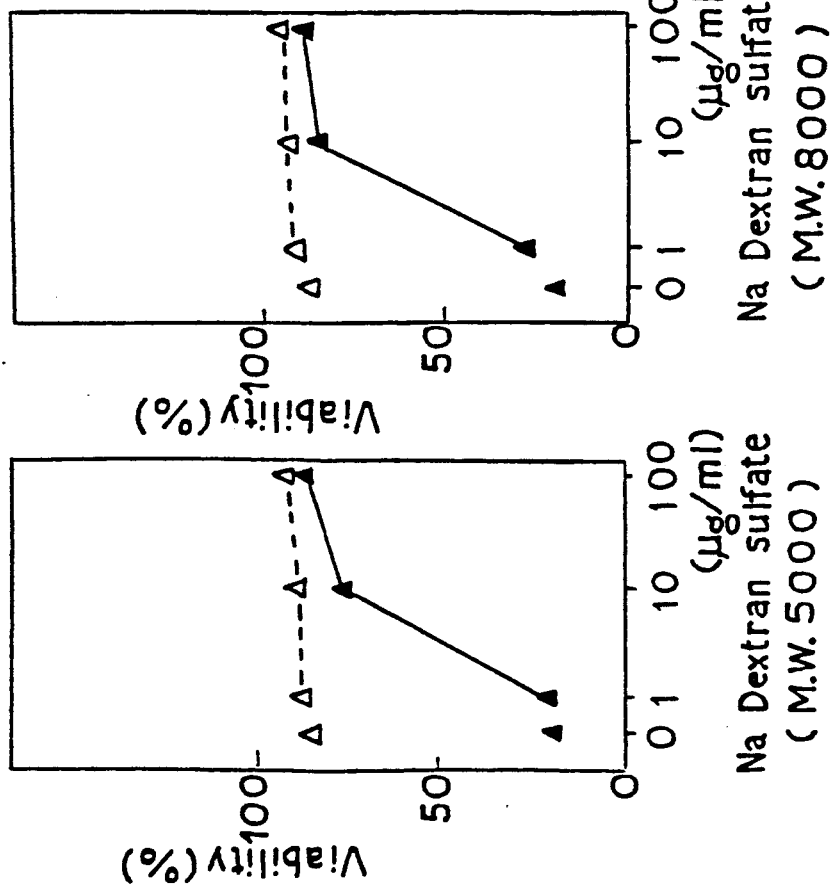
FIG. 16

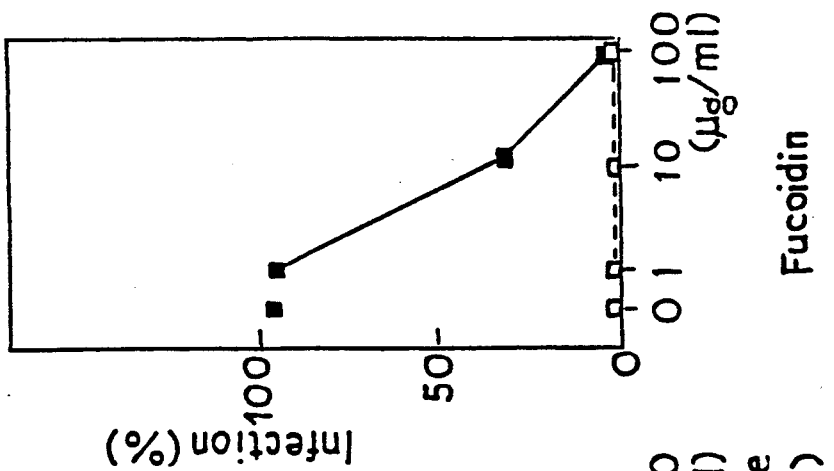
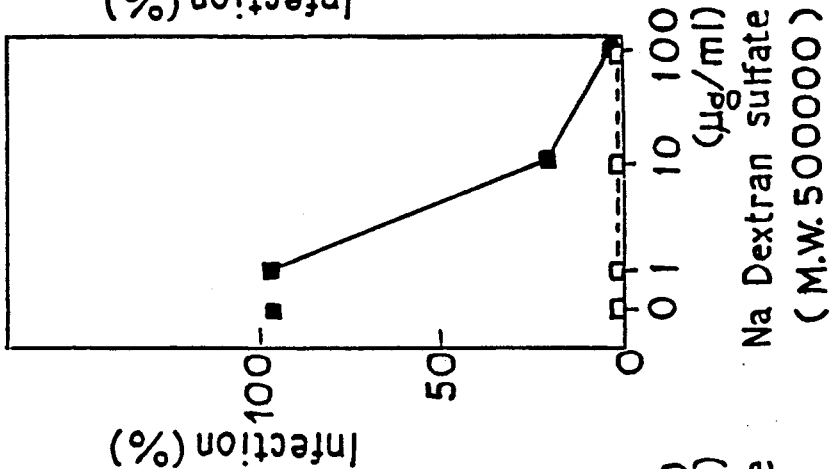
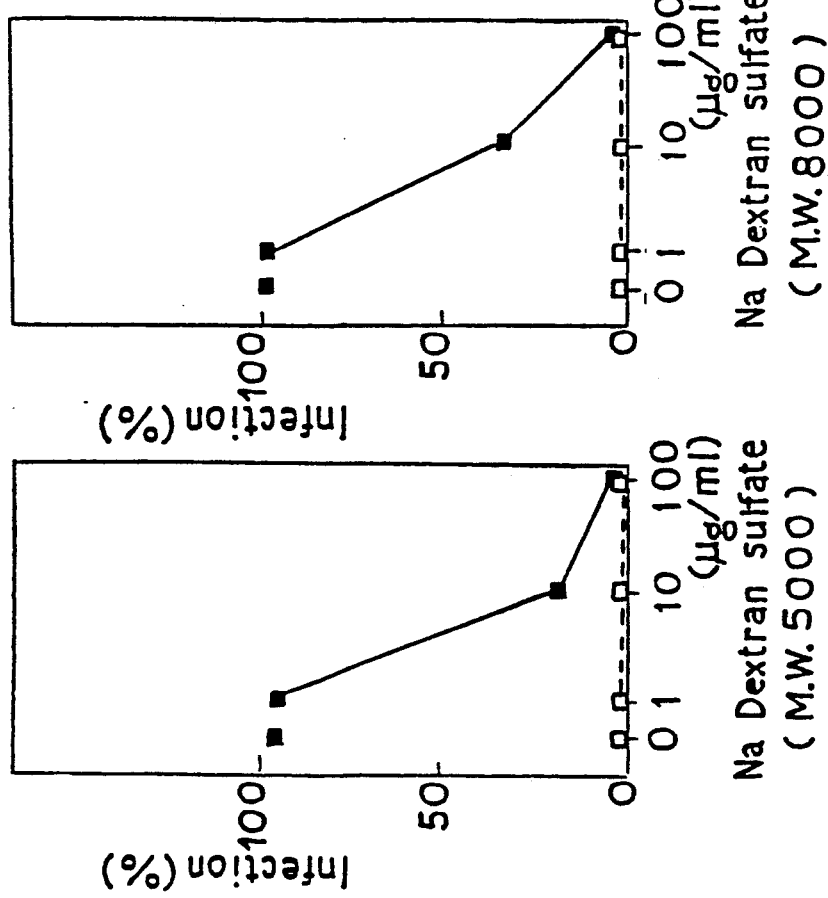
FIG. 23 Na Dextran sulfate (M.W. 5000)
FIG. 24 Na Dextran sulfate (M.W. 8000)
FIG. 25 Na Dextran sulfate (M.W. 500000)
FIG. 26 Fucoidin

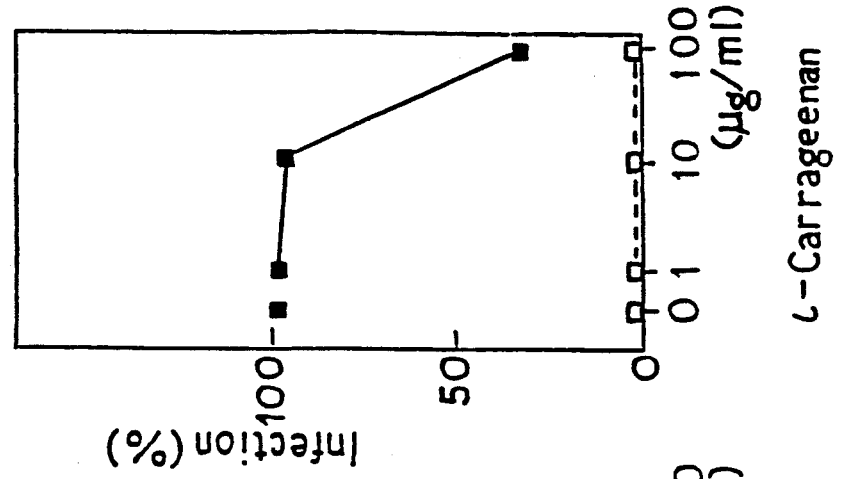
FIG. 29 ι-Carrageenan
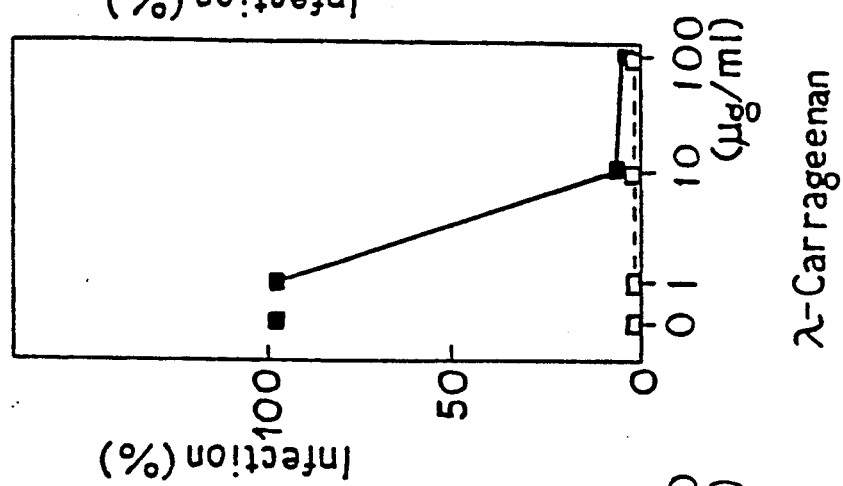
FIG. 28 λ-Carrageenan
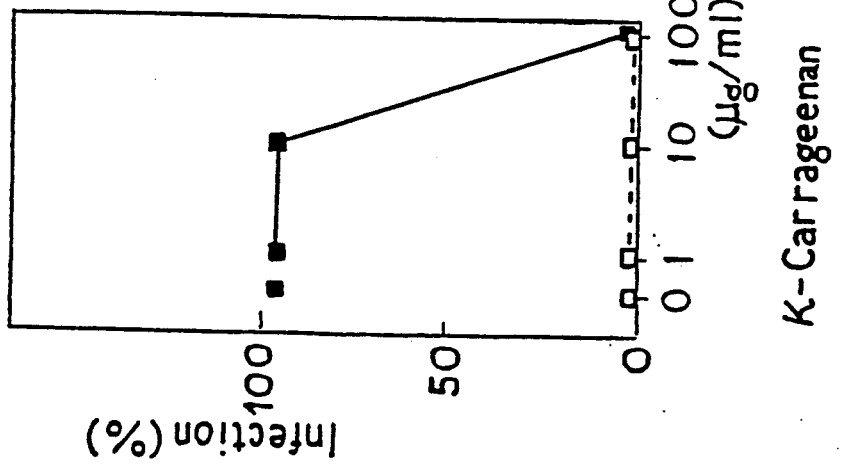
FIG. 27 κ-Carrageenan

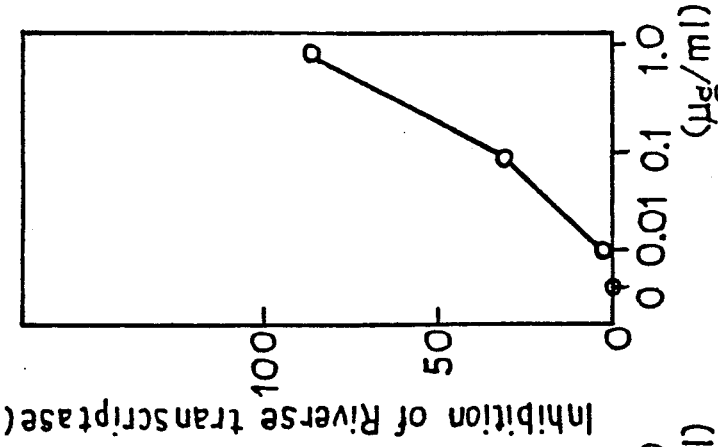
FIG. 30 Na Chondroitin sulfate
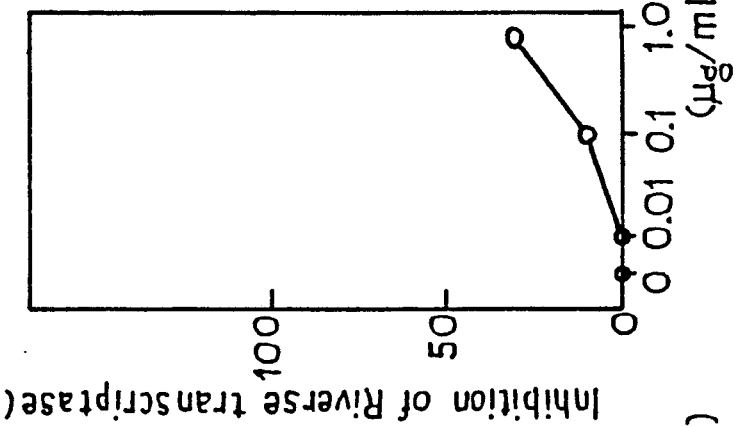
FIG. 31 Na Chondroitin polysulfate
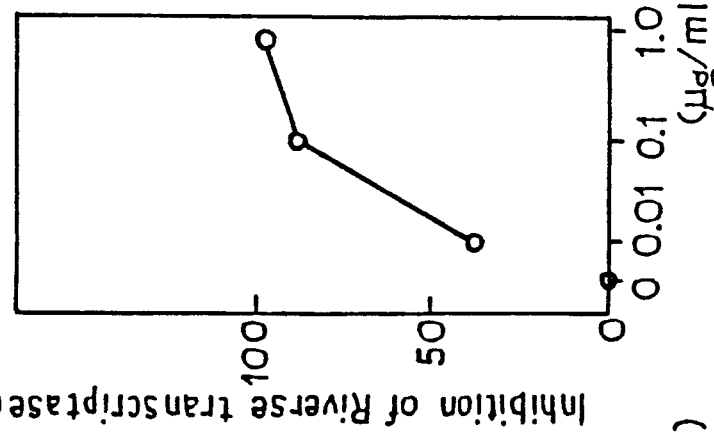
FIG. 32 Na Keratan sulfate
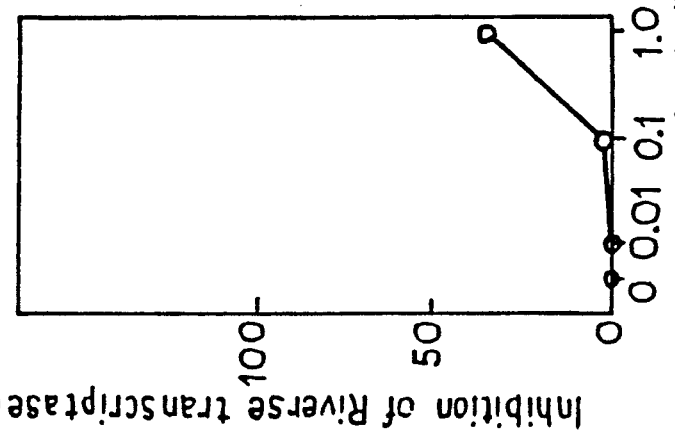
FIG. 33 Na Keratan polysulfate

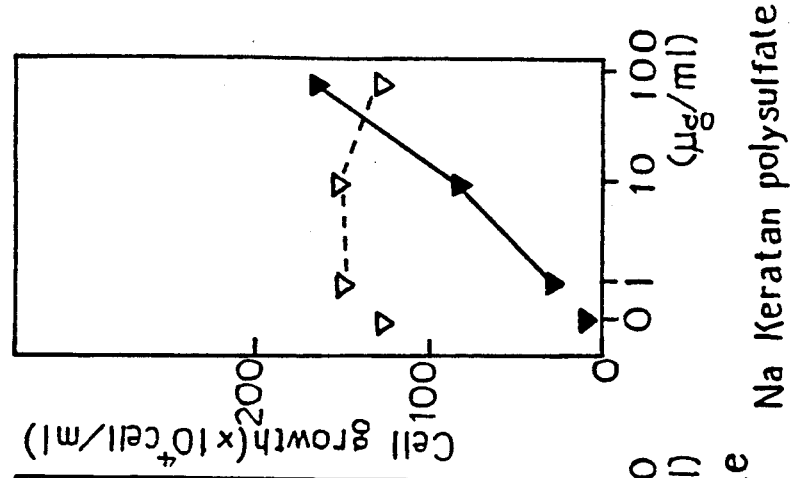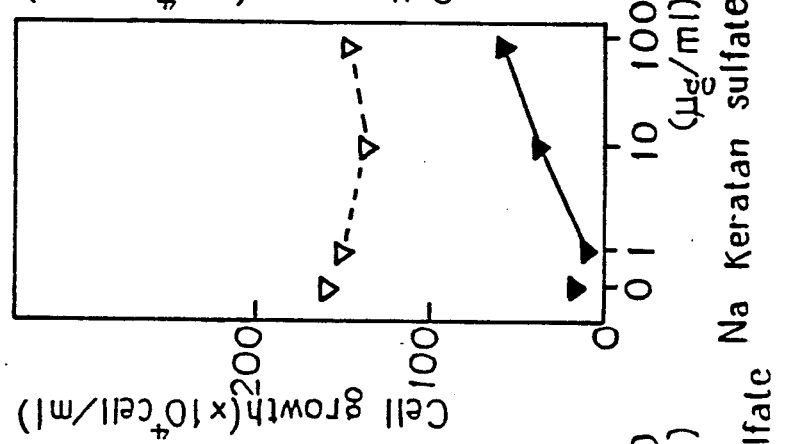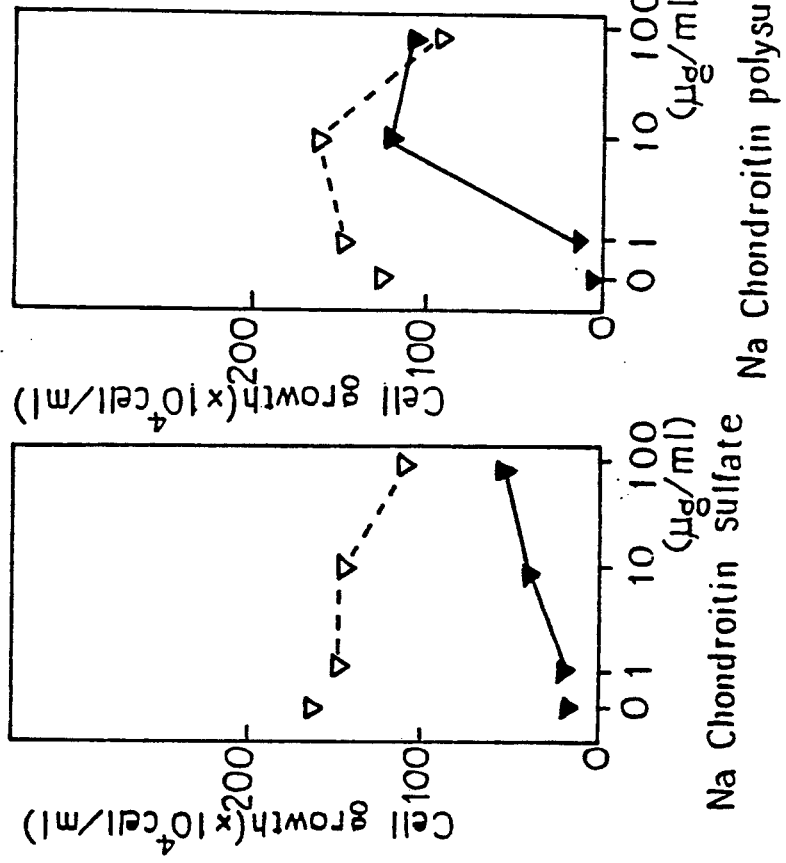

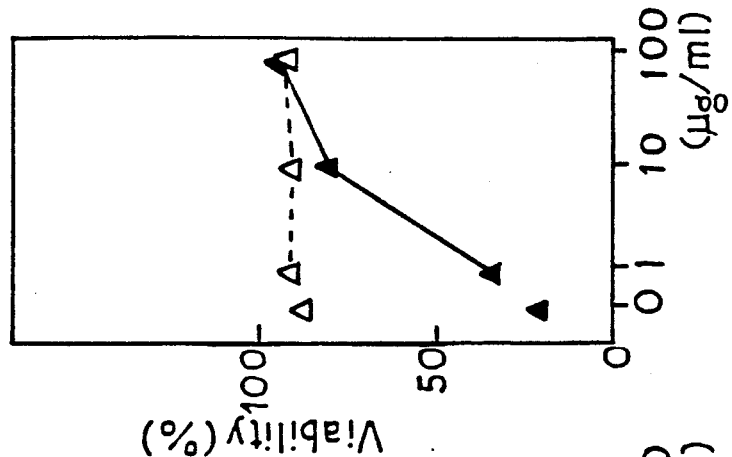
FIG. 41
FIG. 40
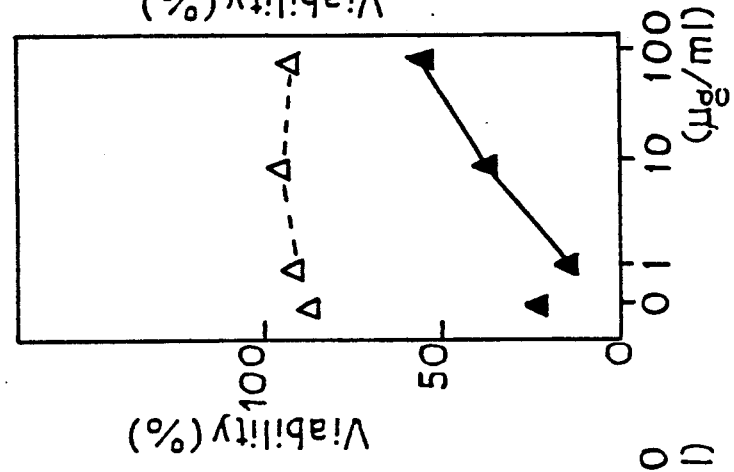
FIG. 39
FIG. 38
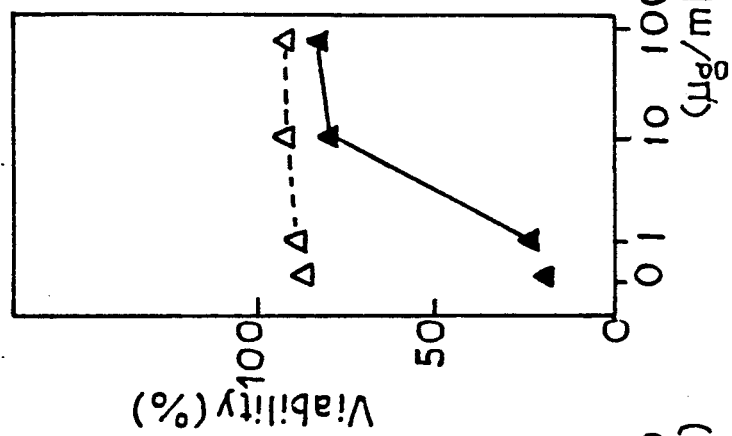
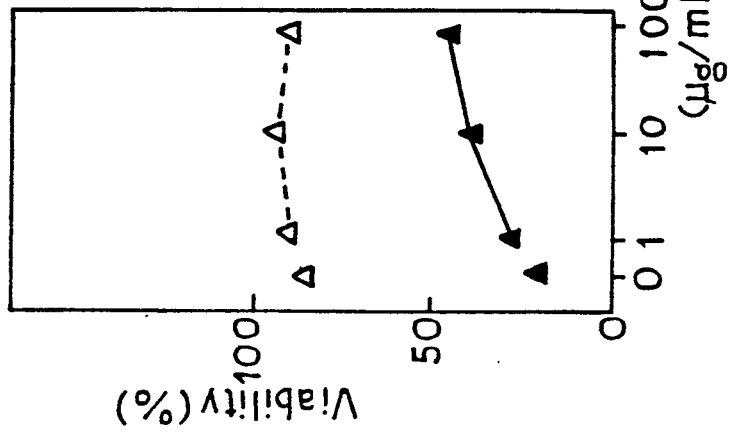

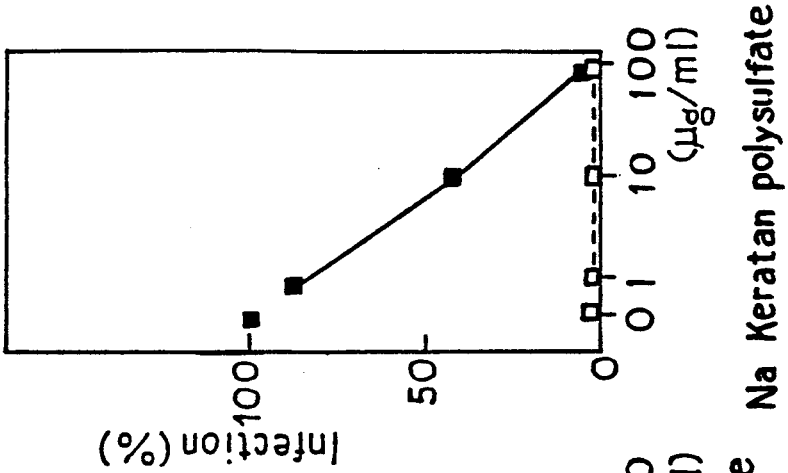
FIG. 45 Na Keratan polysulfate
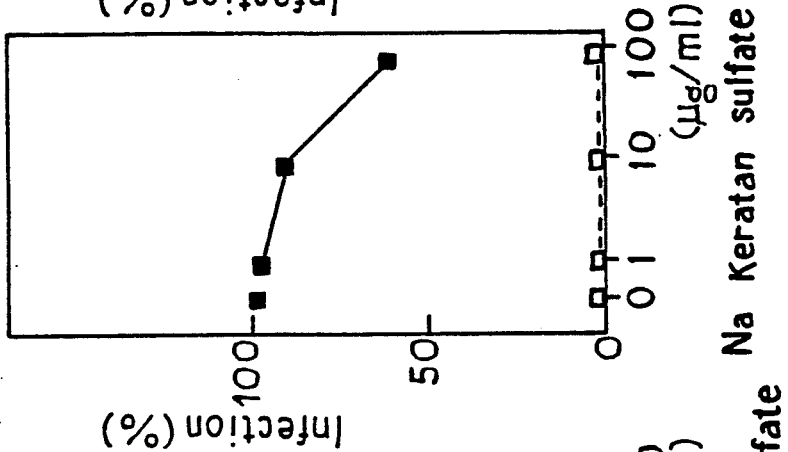
FIG. 44 Na Keratan sulfate
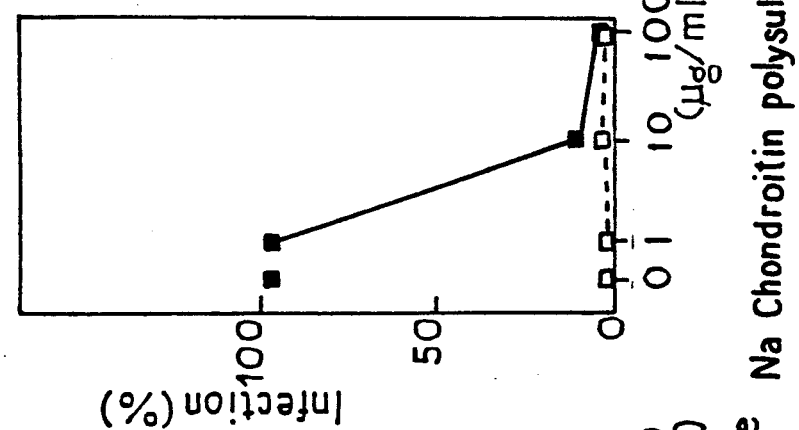
FIG. 43 Na Chondroitin polysulfate
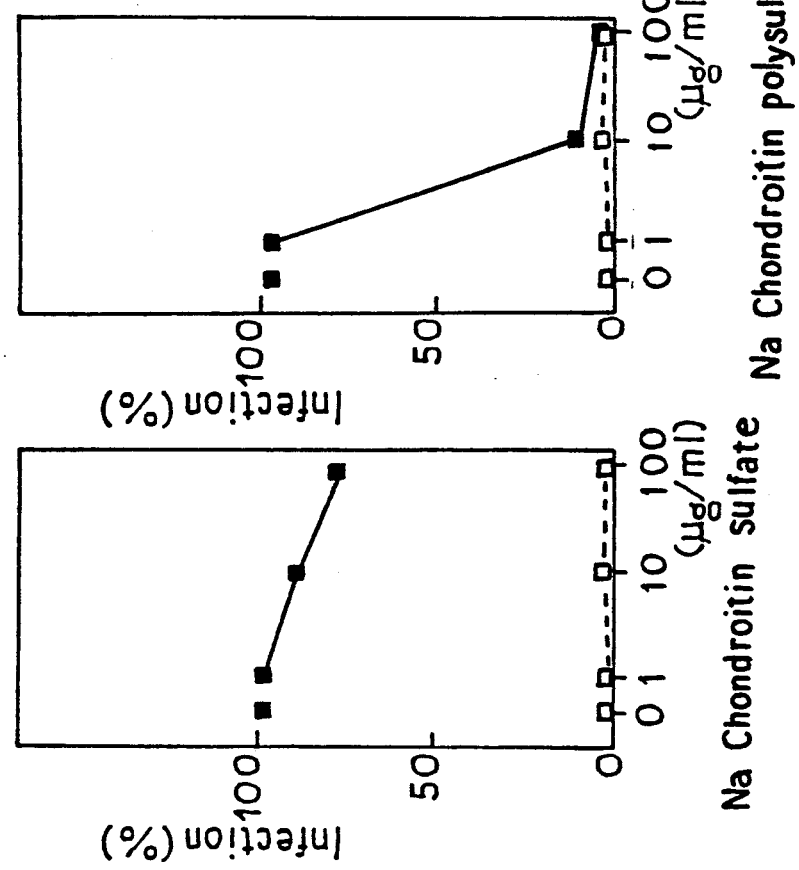
FIG. 42 Na Chondroitin sulfate

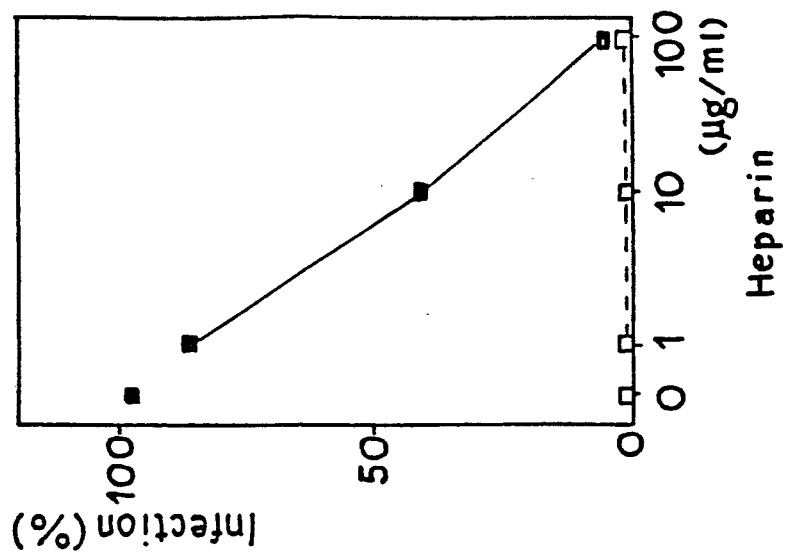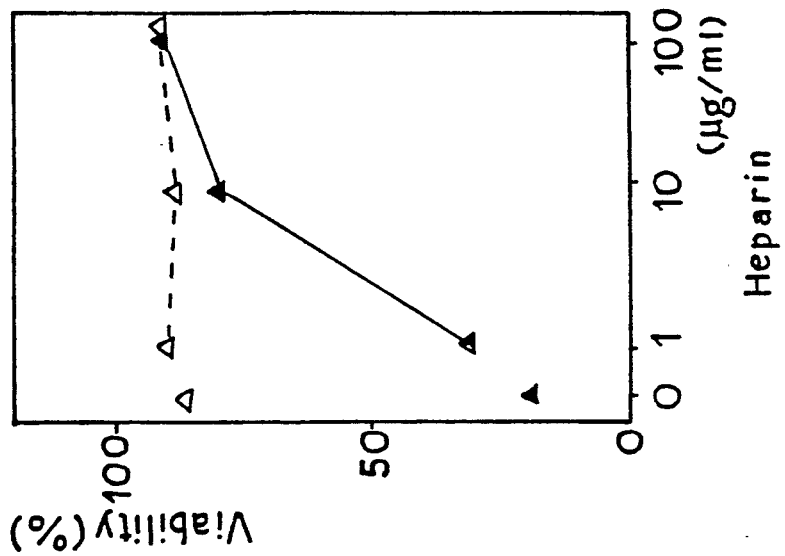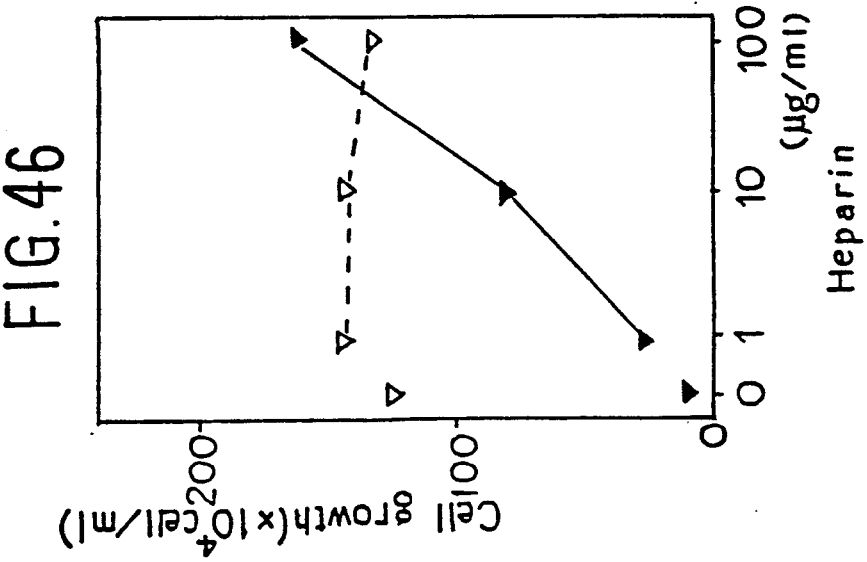

METHOD OF TOPICALLY CLEANSING THE HUMAN BODY

This is a continuation-in-part of application Ser. No. 07/176,065, filed Mar. 31, 1988, now abandoned.

BACKGROUND OF THE INVENTION

1. Field of the invention

The present invention relates to disinfection useful for preventing infection with retroviruses.

More particularly, the present invention relates to a disinfectant composition for retroviruses containing as active ingredient a natural or synthetic oligo- or polysaccharide having at least one S-oxoacid group attached to the saccharic carbon atom through a linking group of lower molecular weight, the manufacture and method of use thereof. The said composition is effective against retroviruses, especially causative viruses for AIDS (acquired immuno deficiency syndrome), ARC(AIDS-related complex), PGL (persistent generalized lymphadenopathy) and LAS (lymphadenopathy syndrome).

Retroviruses refer to a family of viruses which have RNA and reverse transcriptase (RNA-dependent DNA polymerase), of which the latter is essential to the first stage of its self-replication for synthesizing complementary DNA on the base of template RNA of the virus.

Retroviruses include various oncoviruses such as avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, and the like. Among those infective to human, those important are adult T-cell leukemia virus (ATLV), or human T-lymphotropic virus type I (HTLV-I), and type II (HTLV-II). The adult T-cell leukemia abounds in Japan, especially in the west part, but the effective treatment containing prevention and therapeutics of the disease has not been established.

On the other hand, retroviruses also include those having no oncogenecity, such as visna virus, ovine progressive pneumonia virus, ovine maedi virus, simian T-lymphotropic virus type III (STLV-III), equine infectious anemia virus, and the like. The viruses isolated from human as causative agents for AIDS, ARC, PGL and LAS (so-called AIDS-viruses such as HTLV-III, LAV1, LAV2, ARV and HTLV-IV) belong to this subfamily. Recently, AIDS-causative viruses are called HIVs (human immuno deficiency viruses).

Further, as the third subfamily, there is known a spumavirinae to which simian foaming virus belongs. Also, a retrovirus has been isolated recently as a causative virus for Kawasaki disease (mucocutaneous lymphonode syndrome).

World-wide interests have been focused on AIDS due to its unfavorable prognosis. It is a clinical syndrome characterized by recurrent oppotunistic infections, (e.g. pneumocystis carinii pneunonia, cryptococcal meningitis, disseminated toxoplasmosis), lymphadenopathy, and an aggressive Kaposi's sarcoma, and induces a high mortality more than 90% by the dysregulation of immune system. It is also known that the helper-T cells are specifically destroyed by the infection of the virus. Further, among the conditions related with AIDS viruses, there are a carrier who exhibits no disease conditions, PGL (persistent generalized lymphadenopathy), LAS (lymphadenopathy syndrome), ARC-(AIDS-related complex), etc.

In order to find out substances effective against causative viruses for AIDS, PGL, LAS and AIDS-virus carrier, the present inventors, using a cell line of MT-4 established from T-cells of adult T-cell leukemia patient and HTLV-III which is a causative virus for AIDS, examined the effects of various substances on the infection and replication of HTLV-III.

The above MT-4 cell line is absolutely susceptible to the infection with HTLV-III which causes and followed by cell lysis (experimental HTLV-III infection). The present inventors found that when certain polysaccharides having a sulfonate group ($-SO_3^-$) or mucopolysaccharides having a sulfonate group or the sulfuric acid esterified substances thereof were added to the experimental HTLV-III infection system, the infection of HTLV-III on MT-4 cells and viral replication were strongly inhibited without accompanying any toxicity to the cells.

Further, the present inventors demonstrated that the above polysaccharides inhibit the reverse transcriptase of the retroviruses including AIDS virus in vitro, prevent the adsorption of such viruses to the target cells and inhibit cell fusion of virus-infected cells to noninfected cells, thereby suppressing the replication of the virus.

2. Description of related art

Among the sulfuric acid esters of polysaccharides, dextran sulfate having a lower molecular weight has long been commercially available as an antilipemic or anti-arteriosclerosis agent. Also, dextran sulfate having a relatively higher molecular weight is known to have an inhibitory action against herpes virus. (European Patent Publication No.0066379). However, since the herpes virus is a DNA virus, its replication is absolutely different from that of the retrovirus which depends entirely on reverse transcriptase for synthesis of DNA. Accordingly, the effectiveness of dextran sulfate on herpes virus does not necessarily mean its effectiveness on retrovirus. Furthermore, dextran sulfate having a lower molecular weight less than 10,000 was found to be almost ineffective on herpes viruses.

Among the mucopolysaccharides or these sulfates, chondroitin sulfate is commercially available as a drug for sensorineural hearing impairment, neuralgia, lumbago and chronic nephritis, and also as a cornea-protective ophthalmic solution. Keratan sulfate is obtainable from the cartilage, teichuronic acid from the cell walls of *Bacillus subtilis*, hyaluronic acid from shark skin, whale cartilage, or from human serum, heparan sulfate from bovine liver or lung, and chitin from arthropod or from fungus or yeast, respectively. The preparation process for the further sulfuric acid esterified compound of chondroitin sulfate is described in Japanese Patent Publication (JP, B2) No.9570/1971.

Heparin is known to inhibit various enzymes in vitro, e.g., DNA polymerase of phytohemagglutinin stimulated human lymphocytes and reverse transcriptase of simian sarcoma virus (Cancer Research, 38, 2401 2407), but is not proved to inhibit the viral infection of cells.

SUMMARY OF THE INVENTION

In a first aspect, the present invention provides a disinfectant composition for retroviruses comprising as an effective ingredient a natural or synthetic oligo- or polysaccharide having at least one S-oxoacid group attached to the saccharic carbon atom through a linking group of lower molecular weight.

In a second aspect, the present invention provides a use of a natural or synthetic oligo- or polysaccharide having at least one S-oxoacid group attached to the saccharic carbon atom through a linking group of lower molecular weight for the manufacture of a disinfectant composition for controlling retroviruses.

In is third aspect, the present invention provides a method of disinfection for retroviruses which comprises contacting inanimate object in need of such treatment with a natural or synthetic oligo- or polysaccharide having at least one S-oxoacid group attached to the saccharic carbon atom through a linking group of lower molecular weight.

BRIEF EXPLANATION OF THE DRAWINGS

FIGS. 1-7 show the reverse transcriptase inhibition activities of the test substances in Example 1.

FIGS. 9-15, 16-22, and 23-29 show the effects of the test substances on cell growth, viability, and infected cell rate(%), of MT-4 cells infected with HTLV-III, respectively, in Example 3.

FIGS. 30-33 show the reverse transcriptase inhibition activities of the test substances in Example 5.

FIGS. 34-37, 38-41, 42-45 show the effects of the test substances on cell growth, viability, and infected cell rate(%) of MT-4 cells infected with HTLV-III, respectively, in Example 6.

FIGS. 46, 47 and 48 show the effects of heparin on cell growth, viability and infected cell rate(%) of MT-4 cells infected with HTLV-III, respectively, in Example 7.

DESCRIPTION OF THE PREFERRED EMBODIMENT

Figure 8:
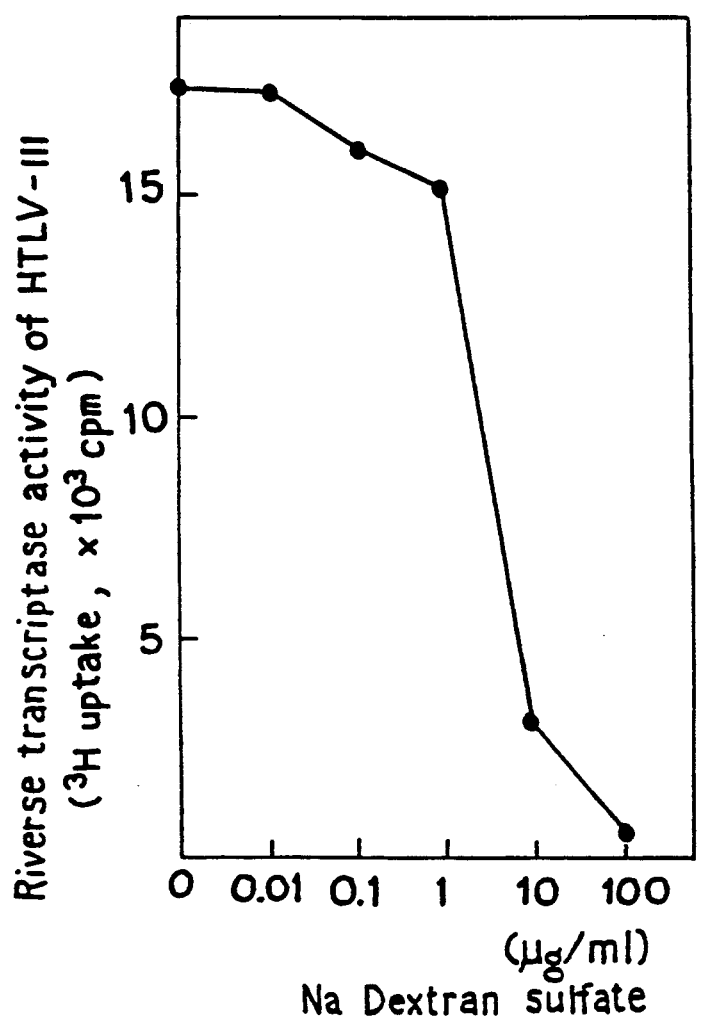
FIG. 8 shows the reverse transcriptase inhibition activity of the test substance in Example 2.
Figure 15:
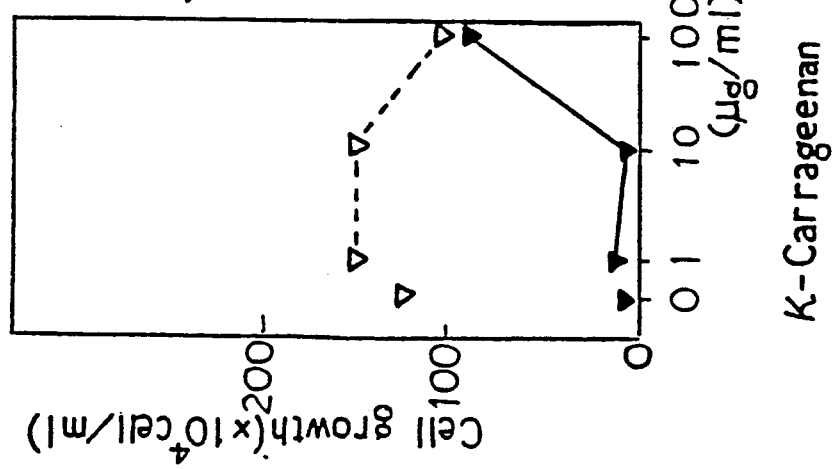
Figure 14:
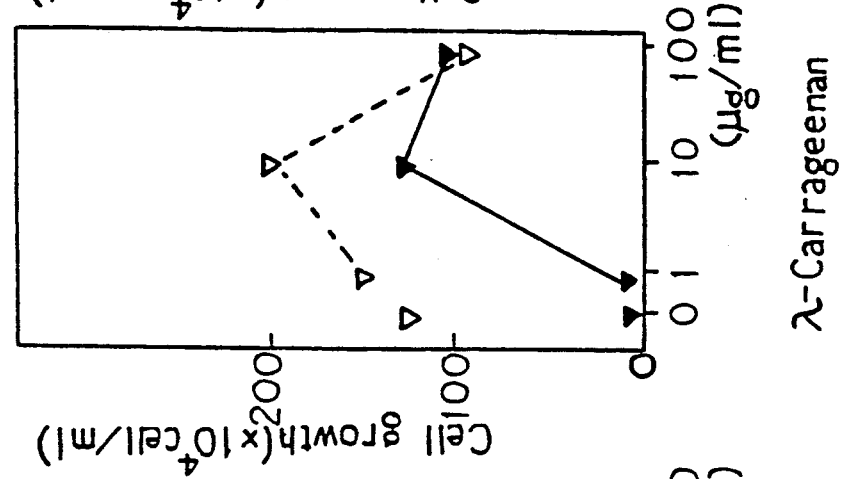
Figure 13:
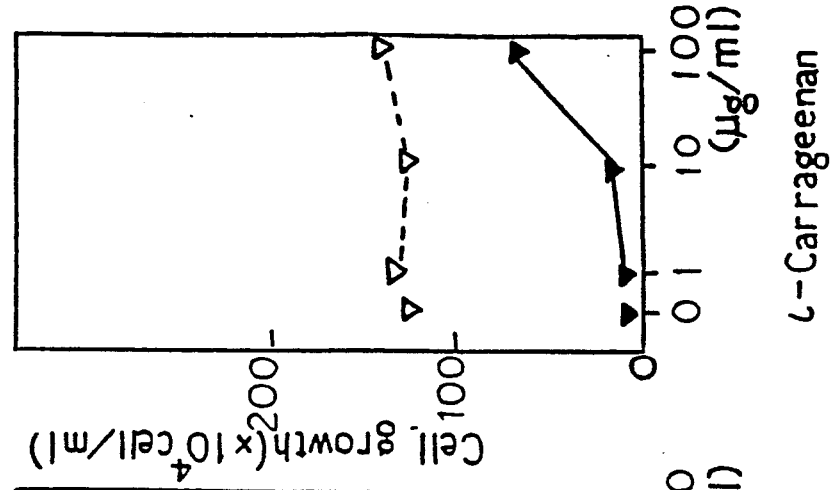
Figure 20:
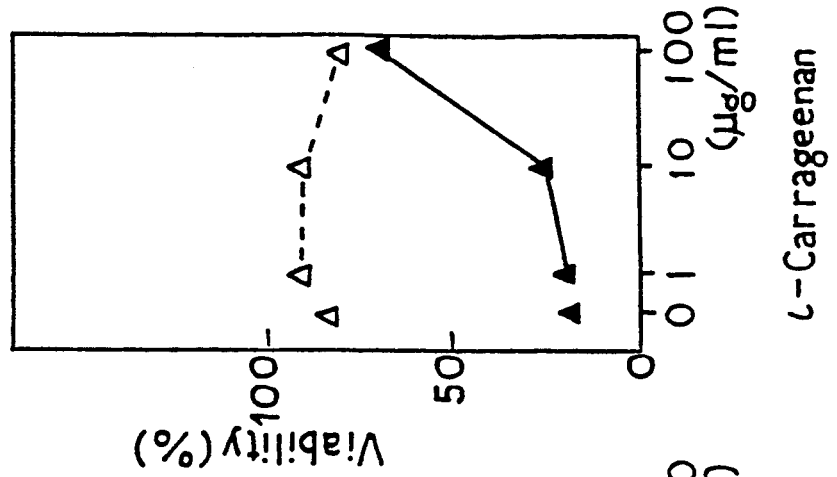
Figure 21:
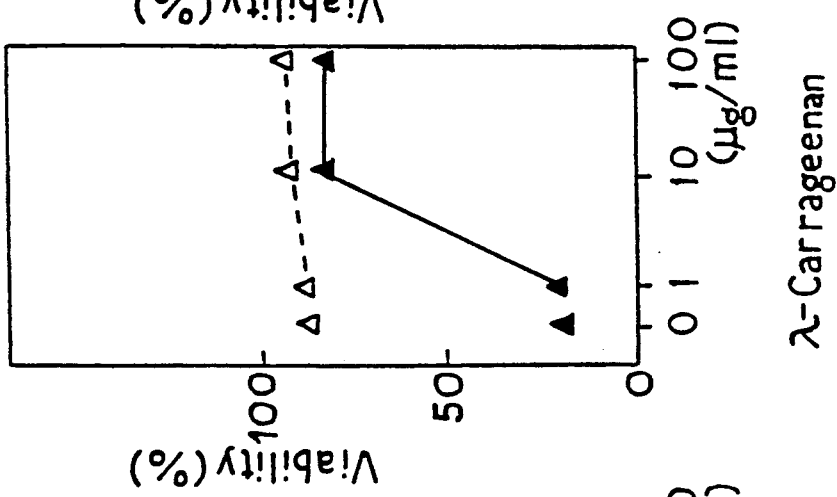
Figure 22:
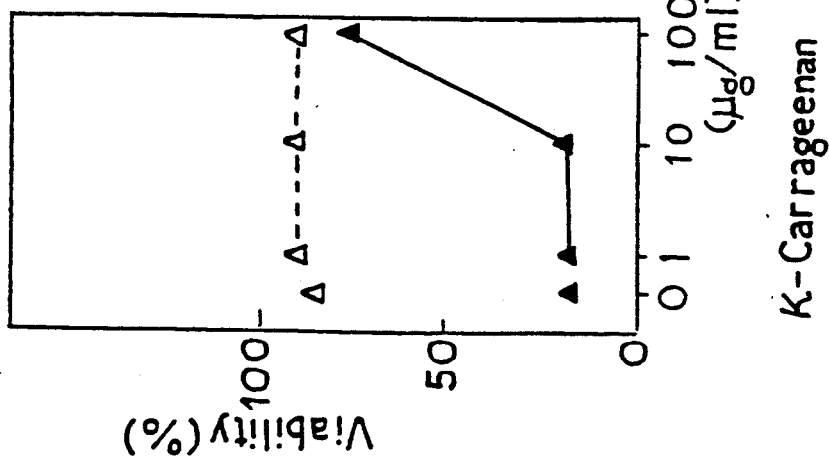

The term "disinfection" or "disinfectant" herein is intended to cover all prevention for infection including deactivation, elimination, inhibition of inter-cellular transfer, and extermination of viruses, as well as cleansing.

The retroviruses includes all viruses having RNA and reverse transcriptase as the basic components including those exemplified above.

The disinfectant composition or the method of disinfection herein are applied to all inanimate objects including instruments, and intended to be performed for purposes other than application of a pharmaceutical composition to human or animal bodies. The inanimate objects referred to herein include textile sanitary materials (e.g., absorbent cotton, gauze, bandage, textile sanitary supplies, mask, eye band, triangle bandage, cotton stick, etc.), medical and sanitary rubber articles (rubber gloves for surgical operation, contraceptive sheath, rubber nipple, etc.), food processing instruments, office appliances, medical, dental or veterinary instruments (e.g., surgical bed, anesthetic instrument, artificial heart-lung instrument, chiropractic instrument, needle, ophthalmic instrument, dental treating table, artificial insemination instrument for kettle, retainer for exclusive use for animal, etc.), furniture, fixtures, and indoor and outdoor fittings (e.g., bed, desk, chair, chest of drawers, sliding paper door (shoji), sliding door (fusuma), door, mat, carpet, curtain, straw mattress (tatami), sink, basin, lavatory stool, bath tub, display case, book case, boot cupboard, umbrella stand, etc.), accessories, cosmetics (e.g., compact, manicure set, toothbrush), smoking goods, toys, wrist watch, glasses, hearing aid, footwear, clothes (e.g., night clothes, pyjamas, working clothes, white overall, school children's uniform, men's wear, ladies' dresses, etc.), bed clothes (e.g., quilts, quilt covers, pillows, pillow covers, sheets, blankets, mattresses, etc.), barber's utensils (e.g., hair clippers, scissors, razor, comb, etc.), interiors of transporting machines (e.g., vessel, aircraft, railway vehicles, automobile, etc.), interior of buildings (e.g., hospital, cinema house, restaurant, etc.), and excrements, service water and sewage, lavatory, interiors of cattle house (e.g., hen house, pigpen, cowshed, etc.), breeding instruments such as poultry cage (for breeding, for egg-laying hen, for broiler), pig breeding cage, feeding passage, food-feeder, water feeder, incubator, etc.), dairy instruments (e.g., milker for milking, teat cup, milk jar, milking bucket, etc.), working clothes (e.g., fatigues, caps, boots, rubber gloves, etc.), and excrement board, sewerage, drainage, etc.

The oligo- or polysaccharide used according to the present invention has at least one S-oxoacid group attached to the saccharic carbon atom through a linking group of lower molecular weight. Such an oligo- or polysaccharide may be natural or synthetic. The term "natural" is intended to mean that the oligo- or polysaccharide is obtainable from a natural source such as a plant, microorganism or animal by extraction and other means. The term "synthetic" is intended to mean that the oligo- or polysaccharide is obtainable synthetically, for example, by introducing an S-oxoacid group into another oligo- or polysaccharide which has or has not a S-oxoacid group and which is natural or unnatural (and synthetic).

The term "oligosaccharide" refers to a carbohydrate containing from two up to about nine monosaccharides linked together. For example, when a oligosaccharide contains three mcnosaccharides, one, two or three of the monosaccharides may have at least one S-oxoacid group.

The term "polysaccharide" refers to a carbohydrate containing about ten or more monosaccharides linked together. At least one and a minor or major part or all of the monosaccharides may have at least one and normally up to four S-oxoacid groups.

The S-oxoacid group includes a sulfo group ($-SO_3H$) and a hydroxysulfinyl group ($-S-.OH$). A preferred S-oxoacid group is a sulfo group.

The term "saccharic carbon atom" refers to a carbon atom which is a member of tetrahydrofuran or tetrahydropyran ring of a monosaccharide contained in the oligo- or polysaccharide.

The linking group of lower molecular weight includes oxy ($-O-$), imino ($-NH-$), thio ($-S-$), methylene ($-CH_2-$), ethylidene ($-CH(CH_3)-$) groups and the like. The term "lower molecular weight" is intended to mean that the group has a molecular weight from about 14 up to about 32. Preferred linking groups are oxy and imino groups.

One class of the oligo- or polysaccharide is natural polysaccharides having at least one hydrogen sulfate group (—O—SO$_3$H) and is obtained from a plant or a microorganism, or a synthetic polysaccharide having at least one hydrogen sulfate group (—O—SO$_3$H) and is formed by esterifying a polysaccharide obtained from a plant or microorganism.

Within this class, a preferred subclass is a polysaccharide composed of non-amino monosaccharide a (including sugar acid) as a repeating unit. This polysaccharide, however, may contain a trace amount of nitrogen. Examples of the non-amino sugar repeating units include xylose, arabinose, rhamnose, fucose, glucose, galactose, glucuronic acid, galacturonic acid, mannuronic acid, etc. The natural polysaccharide includes carrageenan (galactan sulfate obtainable from *Gigartina tenella*, etc.) an fucoidin (polyfucose sulfate obtainable from *Laminaria* brown seaweed). Carrageenan includes κ-carragheenan, λ-carrageenan, ι-carrageenan, etc. which have different contents of hydrogen sulfate group. The synthetic polysaccharide includes those to be obtained by sulfuric acid esterification of polysaccharides, e.g., starch and the partial hydrolyzate thereof, dextran which is produced by Leuconostoc sp. and the partial hydrolyzate thereof (usually having the molecular weight of 500–2,000,000, ordinarily 2,000 and 300,000, preferably 2,000–10,000, most suitably 3,000–8,000, e.g., 7,000–8,000), glycogen, pectin, cellulose, plant viscous liquids (gum arabic, tragacant gum, etc.), plant mucilage products (those obtainable from *Hibiscus esculentus, Aloe, Brasenia schreberi*, xylan, etc.), viscous liquids of marine and fresh water algae (alginic acid, laminarin, etc.) or polysaccharides derived from microorganisms (lentinan, pullulan, mannan, etc.). They include known ones (dextran sulfate, cf., European Patent Laid-open Publication No.0066379) and novel ones. The novel ones may be produced in the same manner as the known ones. An example of the preparation process is shown, as follows:

Chlorosulfonic acid is added dropwise to dry pyridin of 8–10 fold volume while cooling. To the mixture are added small amounts of formamide and dextran (about ¼ weight of chlorosulfonic acid), and the mixture is heated to 55°–65° C. under stirring. After stirring the mixture for several hours, the solvent is distilled off, and the residue is purified for example by recrystalization, dialysis, etc. Within the synthetic polysaccharides, those obtained by further sulfuric acid esterification are represented by the term "polysulfate".

Another class of the oligo- or polysaccharides is natural polysaccharides having at least one hydrogen sulfate group (—O—SO$_3$H) and is obtained from an animal, or a synthetic polysaccharide having at least one hydrogen sulfate group (—O—SO$_3$H) and is formed by esterifying a polysaccharide obtained from an animal.

Within this class, a preferred subclass is mucopolysaccharides, which are composed of amino monosaccharides (including N-acyl or NH-SO$_3$H) as a repeating unit. This may further contain as another repeating unit non-amino sugar or an acid derivative thereof. The repeating amino-sugar unit or its N-acylated (preferably N-acetylated) derivatives include glucosamine, galactosamine, N-acetylated derivatives thereof, and the sulfuric acid ester or partial hydrolyzate of the above compound. Examples of the monosaccharide or acid (preferably, hexulonic acid) include glucose, galactose, glucuronic acid, iduronic acid, etc. The mucopolysaccharides containing such repeating unit include heparin, keratan sulfate, chondroitin-4-sulfate, chondroitin-6-sulfate, dermatan sulfate, teichuronic acid, hyaluronic acid, heparitin sulfate, chitin, and their partial hydrolyzates, modified derivatives (e.g., partial acylated products), and synthetic polysacchrides containing the repeating unit such as above.

The mucopolysaccharide polysulfates are defined as the products which are synthesized by additional sulfuric acid esterification of the above mucopolysaccharides having sulfate groups. This esterification may be carried out, for example, according to the procedure described in Japanese Patent Publication No.9570/1971. In general, the esterification is carried out by treatment of the mucopolysaccharides with a sulfating reagent such as concentrated sulfuric acid or chlorosulfonic acid.

These reactions are usually carried out with or without use of a solvent at low temperatures. The reaction product is separated by conventional procedure, e.g., neutralization, concentration, precipitation, recrystallization, chromatography, etc.

The salts of mucopolysaccharides or their sulfates include the salts of an inorganic base such as sodium salt, potassium salt, ammonium salt, etc., and salts of an organic base such as diethanolamine salt, cyclohexylamine salt, amino acid salt, etc. These salts are produced from the corresponding acids by conventional procedures. The above oligo- or polysaccharides and their salts may be used alone or as a mixture with the metal salts such as zinc, aluminum, etc.

The oligo- or polysaccharide should be used in an amount sufficient to produce the desired disinfection/cleansing effect. Such an amount is in general 2.5 to 50,000 ppm or higher, preferably 5 to 30,000 ppm. The application method can be optional such as spraying, dipping, coating, impregnating, etc.

For application, the effective ingredient may be mixed with a carrier for disinfection/cleansing such as organic or inorganic solid or liquid excipients, and applied in the form of a conventional preparation. Such preparation includes liquids (e.g., liquid, emulsion, suspension, etc.), and cream or ointment. The above carriers include water, alcohol, gum arabic, etc. If necessary, auxiliary, stabilizer, emulsifier, lubricant, binder, pH regulating agent, isotonicity agent, and other additives in ordinary use may be added.

Besides, the composition may be used together with another disinfectant or cleanser such as ethanol, isopropanol, formalin, phenol, cresol, oxidol, potassium permanganate, boric acid, sodium hyposulfate, iodine, iodine tincture, iodoform, povidone-iodine, benzothonium chloride, benzalkonium chloride, chlorhexidine gluconate, alkyl polyaminoethyl glycine hydrochloride, polyhexamethylene biguanide hydrochloride, etc.

Also, the composition of the present invention may be applied as being adhered to the surfaces of therapeutic or sanitary rubber products or resin products or impregnation in the material rubber or resin per se.

The toxicity of the above oligo- or polysaccharide is extremely low. For example, the acute toxicity (LD$_{50}$) of sodium dextran sulfate (molecular weight 7,000–8,000, S-content 17–20%) is 21,000 mg/kg and 4,500 mg/kg when administered orally and intravenously to mice, respectively. The acute toxicity (LD$_{50}$) of sodium chondroitin sulfate is 4,000 mg/kg or more and 7,500 mg/kg or more when administered intraperitoneally and orally to mice, respectively. The acute toxicitiy (LD$_{50}$) of sodium heparin is 1,500–2,000 mg/kg when intravenously given to mice.

The disinfectant/cleanser for retrovirus according to the present invention may be used for example for the following purposes:

(1) Deactivation of virus (usable simultaneously with another disinfectants such as alcohol, cresol, etc.):

Disinfection of excretions; disinfection of house, furniture, lavatory, service water and sewerage, garden, road, vacant lot, working place, etc. as disinfectant for public sanitation; disinfection of hospital or research facilities (e.g., surgical operation room, hospital room, laboratory, experimental instrument, clean bench, etc.); disinfection of therapeutic instruments (e.g., instruments for surgical operation, instruments for inspection, dental instruments, opthalmic instruments, instruments for obstetrics and gynecology, endoscope, gastrocamera, contact lens, glasses, etc.); disinfection of therapeutic auxiliaries (e.g., gauze, mask, bandage, nursing nipples, etc.); disinfection of cosmetic goods (e.g., hair clipper, razor, comb, etc.); disinfection of interior of transporting machines (e.g., vessel, aircraft, railway cars, automobile, etc.), interiors of cattle house (e.g., henhouse, pigpen, cowshed, etc.), breeding instrument, disinfection of dairy instruments, etc.

(2) Removal of virus:

Cleansing of the above hospital or research facilities, medical appliances, beauty and hair-dressing instruments, objects set in house or indoors (e.g., furniture, stool in lavatory, etc.), transporting machines, clothes (e.g., white lobe, working clothes including those for livestock farming, underwear, night gown, etc.).

Adsorption to the resin surface or allowing the resin per se to contain (e.g., by causing blood or body fluid to circulate in the circulation apparatus furnished with these resins, the virus present in blood or body fluid is to be adsorbed and removed; or by using an eye band comprising such resins, the virus present in tears is to be adsorbed and removed); attachment to outfittings for surgical operation such as operation wear, cap for operation, mask for operation, gloves for operation, etc.; or allowing the materials per se for these outfittings to contain (disinfection to virus producing cells resulting from unexpected exposure or splashing of blood or body fluid during operation).

(3) Inhibition of inter-cellular transfer:

Addition to preserved blood or blood products, attachment to contraceptive appliance, or allowing the contraceptive appliance material per se to contain (disinfection to virus producing cells in semen or vaginal fluid).

The following examples will illustrate the present invention in further detail.

Preparation 1

Preparation of chondroitin polysulfate from chondroitin sulfate

Chondroitin sulfate (5g) was added to 95% sulfuric acid (10 ml) cooled below $-25°$ C. with stirring. After addition, the reaction mixture was stirred at the same temperature for 90 minutes. After the end of the period, the reaction solution was gradually poured onto ice (120 g) with stirring. To the resulting solution was gradually added calcium carbonate with sufficient stirring. The precipitates were filtered off and washed well with water. To the combined filtrates (240 ml) was added ethanol to the final concentration of 20% (v/v), and the solution was kept to stand overnight at 5° C. to precipitate calcium sulfate. The precipitates were filtered off, and the stirred filtrate was adjusted to pH 10 with sodium carbonate. After addition of acetic acid to make the solution weakly acidic, the solution was concentrated to about 20 ml, then diluted with ethanol (100 ml), and kept to stand overnight at 5° C. The precipitates in the solution were separated by centrifugation, washed with ethanol, then with ether, and dried under reduced pressure to give white powder of the title compound.

Preparation 2

Preparation of keratan polysulfate from keratan sulfate.

Preparation I was repeated except that keratan sulfate (100 mg) was used as a starting material and 1 ml in place of 10 ml of 95% sulfuric acid was used, and there was obtained the subject Keratan polysulfate.

Formulation Example 1

| Sodium dextran sulfate (molecular weight of 6,000–8,000; S-content of 17–20%) | 6 g |
|---|---|
| Water  q.s. to | 1,000 ml. |

Formulation Example 2

| Sodium dextran sulfate (molecular weight of 5,000; S-content of 13–14%) | 6 g |
|---|---|
| Phenol | 20 g |
| Water  q.s. to | 1000 ml. |

Formulation Example 3

| Chitosan | 1 g |
|---|---|
| 10% acetic acid solution | 15 ml |

10% acetic acid solution was added to chitosan to form a solution, followed by adding water q.s. to 1000 ml.

Formulation Example 4

| Sodium salt of chitin sulfate (sulfate of chitin) | 5 mg |
|---|---|
| Water  q.s. to | 1000 ml |

Formulation Example 5

| Sodium salt of chondroitin polysulfate (sulfate of chondroitin sulfate) | 300 mg |
|---|---|
| 70% ethanol | 10 ml |
| Water  q.s. to | 1000 ml. |

Formulation Example 6

| Sodium heparin | 25,000 units |
|---|---|
| Water  q.s. to | 10 ml |

Formulation Example 7

| Sodium dextran sulfate (molecular weight of 6000–8000; S-content of 17–20%) | 10 g |
|---|---|

| -continued | |
|---|---|
| Glycerin | 50 g |
| Purified water | 40 g |

The above components were mixed under stirring according to the conventional process to give a solution (viscosity 20 cps.). The resulting solution was applied to the whole surface of a condom to allow coating.

Formulation Example 8

| Sodium dextran sulfate (molecular weight of 5000; S-content of 13–14%) | 30 g |
|---|---|
| Maltitol | 30 g |
| Purified water | 40 ml |

The above components were mixed under stirring according to the conventional process to give a solution (viscosity 20 cps.). The resulting solution was applied to the whole surface of a condom to allow coating.

Formulation Example 9

| Sodium dextran sulfate (molecular weight of 50000; S-content 15–16%) | 3 g |
|---|---|
| Purified water | 7 ml |
| Silicone oil | 90 g |

Sodium dextran sulfate was dissolved in purified water, and the resulting solution was gradually added to silicone oil. The mixture was homogenized at 9000 rpm to give an emulsion (viscosity, 150 cps.). This emulsion was extremely stable, hardly undergoing change when subjected to sonic treatment. The resulting emulsion was applied inside the peripheral part of a condom formed by the conventional method and rolled in an annular shape. The emulsion gradually permeated and eventually spread over the whole surface to coat the condom.

Formulation Example 10

Pelletized crude soap(100 parts, prepared from a mixture of beaf tallow and coconut oil by saponification with sodium hydroxide) was admixed under stirring with sodium dextran sulfate (0.5 part; molecular weight of about 8000; S-content of 17%), as well as a suitable amount each of a perfume, colorant(red), paraben, squalene and dipotassium glycyrrhetinate dispersed in a small valume of water. Then, the mixture was roller-kneaded uniformaly, and formed into a rod form by vacuum extruder, followed by stamping to give solid soap.

Formulation Example 1

Crude potassium soap was prepared by reacting a fatty acid mixture containing lauric acid, myristic acid, palmitic acid, etc. with potassium hydroxide. The obtained soft soap (100 parts) was admixed with sodium dextran sulfate (0.5 part, molecular weight of about 8000; S-content of 17%) as well as a suitable amount each of a perfume, colorant, paraben and jojoba oil dispersed in water. Then a required amount of carboxymethyl cellulose was added to the mixture for thickening to give liquid soap.

Formulation Example 12

Sodium polyoxyethylenelaurylether sulfate was thickened with an appropriate amount of laurylamide and admixed with sodium dextran sulfate (at a ratio of 0.2% of the finished product; molecular weight of about 8000; S-content of 17%) as well as a suitable amount each of squalene, dipotassium glycyrrhetinate, paraben, perfume and colorant(yellow) dispersed in water, followed by stirring to give shampoo.

The products of above Formulation Examples 10–12 can also be used as topical cleansing agents for the human body, especially in situations where one may have come into contact with a human retrovirus, such as HIV. Thus, these products will find utility where researchers might accidentally contact HIV, in hospitals, homes and other locations where one might contact body fluid containing HIV and so on. The cleansing vehicle base is not limited, and can be in the form of foams, shampoos, liquid soaps, solid soaps and so on. The following Formulation Examples 13–21 are examples of other cleansing agent products for topical use on humans.

Formulation Example 13 (a scrub-including washing foam)

| Composition (in percent) | |
|---|---|
| 1. potash soap | 37.8 |
| 2. myristic acid | 3 |
| 3. stearic acid | 2 |
| 4. EDTA salt | 0.05 |
| 5. pyrrolidone carboxylate (60%) | 1.0 |
| 6. propylene glycol | 4.4 |
| 7. glycerol | 4.4 |
| 8. lauryldimethylamine oxside (35%) | 4 |
| 9. dipotasium glycyrrhizinate | 0.05 |
| 10. Sodium dextran sulfate | 0.2 |
| 11. scrub | 5.5 |
| 12. perfume | 0.5 |
| 13. water    q.s. to | 100 |

Preparation

A) Components 1 to 9 are combined and warmed to dissolve homogeneously.

B) Components 9 and 10 are dissolved into Component 13.

C) After adding B to A, the mixture of A and B are cooled.

D) When C is cooled to the temperature of 50° C., compositions 11 and 12 are added to the mixture is cooled to 30° C.

E) D is taken out to fill up the container. The above washing foam was used for washing hands and face.

Formulation Example 14 (washing foam)

| Composition (in percent) | |
|---|---|
| 1. potash soap | 37.8 |
| 2. myristic acid | 3 |
| 3. stearic acid | 2 |
| 4. EDTA salt | 0.05 |
| 5. pyrrolidone carboxylate (60%) | 1.0 |
| 6. propylene glycol | 4.4 |
| 7. glycerol | 4.4 |
| 8. lauryldimethylamine oxside (35%) | 4 |
| 9. dipotasium glycyrrhizinate | 0.05 |
| 10. Sodium dextran sulfate | 0.2 |
| 11. perfume | 0.5 |
| 12. water    q.s. to | 100 |

Preparation

A) Components 1 to 9 are combined and warmed to dissolve homogeneously.

B) Components 9 and 10 are dissolved into Component 13.

C) After adding B to A, the mixture of A and B is cooled.

D) When C is cooled to the temperature of 50° C., compositions 11 and 12 are added to and the mixture is cooled to 30° C.

E) D is taken out to fill up the container.

The above washing foam was used for washing hands and face.

Formulation Example 15 (clear-typed soap 1)

| Composition (in percent) | |
|---|---|
| 1. soap base | 59 |
| 2. glycerol | 6 |
| 3. EDTA salt | 0.1 |
| 4. sucrose | 10 |
| 5. Sodium dextran sulfate | 0.2 |
| 6. perfume | 0.5 |
| 7. ethanol | 21 |
| 8. water q.s. to | 100 |

Preparation

A) Components 1 to 9 are combined and warmed to dissolve.

B) A is coated in a mold and it is cooled to form a cake.

C) After B is dried to form a solid at a room temperature, it is cut into a certain shape to obtain clear-typed soaps.

The above soap was used for washing hands.

Formulation Example 16 (clear-typed soap 2)

| Composition (in percent) | |
|---|---|
| 1. soap base | 59 |
| 2. glycerol | 6 |
| 3. EDTA salt | 0.1 |
| 4. sucrose | 10 |
| 5. Sodium dextran sulfate | 0.2 |
| 6. natural jojoba oil | 0.2 |
| 7. perfume | 0.5 |
| 8. ethanol | 21 |
| 9. water q.s. to | 100 |

Preparation

A) Components 1 to 9 are combined and warmed to dissolve.

B) A is casted in a mold and it is cooled to form a cake.

C) After B is dried to form a solid at a room temperature, it is cut into a certain shape to obtain clear-typed soaps.

The above soap was used for washing hands.

Formulation Example 17 (clear-typed soap 3)

| Composition (in percent) | |
|---|---|
| 1. soap base | 59 |
| 2. glycerol | 6 |
| 3. EDTA salt | 0.1 |
| 4. sucrose | 10 |
| 5. Sodium dextran sulfate | 0.2 |
| 6. propylene glycerol | 0.2 |
| 7. perfume | 0.5 |
| 8. ethanol | 21 |
| 9. water q.s. to | 100 |

Preparation

A) Components 1 to 9 are combined and warmed to dissolved.

B) A is casted in a mold and it is cooled to form a cake.

C) After B is dried to form a solid at a room temperature, it is cut into a certain shape to obtain clear-typed soaps.

The above soap was used for washing hands.

Formulation Example 18 (toilet soap)

| Composition (in percent) | |
|---|---|
| 1. soap base | 59 |
| 2. Sodium dextran sulfate | 0.2 |
| 3. clay | 10 |
| 4. perfume | 0.5 |
| 5. water q.s. to | 100 |

Preparation

A) Components 1 to 4 are combined and warmed to dissolve, and then mixed in a kneader.

B) A is extruded in the form of a stick with extruder.

C) After B is stamped out with a metal mold into a certain shape to obtain soaps.

The above soap was used for washing hands.

Formulation Example 19 (sheet soap)

| Composition (in percent) | |
|---|---|
| 1. soap base | 59 |
| 2. EDTA salt | 0.1 |
| 3. Sodium dextran sulfate | 0.2 |
| 4. perfume | 0.5 |
| 5. water q.s. to | 100 |

Preparation

A) Components 1 to 4 are combined and warmed to dissolve.

B) A is poured onto a metal dish to form a sheet of 0.2 to 1 mm in thickness and it is cooled to solidify and dry.

C) After B is taken out, it is cut into a certain size of 2 to 10 cm in length and 2 to 10 cm in width to obtain sheet soaps.

The above soap was used for washing hands.

Formulation Example 20 (medicated soap 1)

| Composition (in percent) | |
|---|---|
| 1. soap base | 59 |
| 2. glycerol | 6 |
| 3. EDTA salt | 0.1 |
| 4. sucrose | 10 |
| 5. Sodium dextran sulfate | 0.2 |
| 6. o-phenylphenol | 3 |
| 7. perfume | 0.5 |
| 8. ethanol | 21 |
| 9. water q.s. to | 100 |

A) Components 1 to 9 are combined and warmed to dissolve, them mixed in a kneader.

B) A is extruder in the form of a stick with extruder.

C) After B is stamped out, it is dried to obtain soaps.

The above soap was used for washing hands.

Formulation Example 21 (medicated soap 2)

| Composition (in percent) | |
|---|---|
| 1. soap base | 59 |

-continued

| Composition (in percent) | |
|---|---|
| 2. glycerol | 6 |
| 3. EDTA salt | 0.1 |
| 4. sucrose | 10 |
| 5. Sodium dextran sulfate | 0.2 |
| 6. 2,4,4'-trichrolo-2-hydrophenyl ether | 1.5 |
| 7. perfume | 0.5 |
| 8. ethanol | 21 |
| 9. water q.s. to | 100 |

A) Components 1 to 9 are combined and warmed to dissolve, then mixed in a kneader.

B) A is extruded in the form of a stick with extruder.

C) After B is stamped out with a metal mold into a certain shape, it is dried to obtain soaps.

The above soap was used for washing hands.

In the above Formulation Examples 13, 15, 18, 19 and 20, the dextran sulfate has a molecular weight of 7,000–8,000 and an S-content of 17–20%; in Formulation Examples 14 and 16, the dextran sulfate has a molecular weight of 5,000 and an S-content of 13%; and in Formulation Examples 17 and 21, the dextran sulfate has a molecular weight of 8,000 and an S-content of 14%

EXAMPLE 1

(Inhibition of reverse transcriptase activity)

Test substances were assayed for inhibition against the enzyme activity of reverse transcriptase (authentic sample) derived from Avian Myeloblastosis Virus (abbrev. AMV), a kind of retrovirus. Five microliters of $(\gamma A)_n$(template RNA), 4 $\mu$l of $(dT)_{12-18}$(primer DNA), and 1 $\mu$l of water were mixed with 5 $\mu$l of 0.5M Tris-HCl (pH 8.4) including 0.1% triton X-100, 5 $\mu$l of lnM-MgCl$_2$, 5 $\mu$l of 20 mM-DDT, 5 $\mu$l of water, and [$^3$H]-TTP (tritium labeled thymidine triphosphate). To this mixture, test substances in solutions (final concentrations: 1, 0.1, and 0.01 $\mu$g/ml, 5 $\mu$l) or buffer solutions (control, 5 $\mu$l) at various doses were added. Then, 5 $\mu$l (one unit) of the authentic reverse transcriptase derived from AMV was added and the reaction mixture was incubated at 37° C. for 30 minutes. The reaction was stopped by addition of trichloroacetic acid, and after filtering the reaction mixture, the radioactivity of the polymerized (3H-T)n retained on the filter was measured using a liquid scintillation counter. As the test substances, sodium dextran sulfate (molecular weight: 5000), same (molecular weight: 8000), same (molecular weight: 500000), fucoidin, $\kappa$-carrageenan, $\lambda$-carrageenan, and $\iota$-carrageenan were used. The results are shown in FIGS. 1–7.

FIGS. 1–7 show that the enzyme inhibition increases with increasing doses of the above test substances.

EXAMPLE 2

(Inhibition of reverse transcriptase activity)

The assay procedure of Example 1 was repeated using disrupted HTLV-III virions as a crude reverse transcriptase in order to evaluate the reverse transcriptase inhibitory effect of dextran sulfate (DS, molecular weight 7,000–8,000, S-content 17–20%). The result is shown in FIG. 8.

FIG. 8 shows that DS has an inhibitory effect against the reverse transcriptase derived from AIDS-virus, HTLV-III.

EXAMPLE 3

(Anti-AIDS virus activity)

To MT-4 cells ($30 \times 10^4$/ml) cultured in RPMI-1640 medium containing 10% bovine serum, was inoculated HTLV-III, and the suspension was incubated at 37° C. for 1 hour to cause the adsorption of the virus. The cell:virus ratio was 500:1. The cells were then washed, and cultured with or without various doses of the test substances (same as those of Example 1) at 37° C. under 5% $CO_2$ for 3 days, after which cell growth, viability, and percentage of infected cells were recorded. The infected cells were distinguished from the uninfected cells by an indirect immuno-fluorescence method. Thus, the cultured cells were fixed with cold methanol on a slide glass, reacted with antibody to the HTLV-III-specific antigens, and further with the secondary antibody (having a fluororescent label). The results are shown in FIGS. 9–29, wherein, $\nabla$, $\Delta$ and $\square$ show the controls without virus, ▼, ▲ and ■ show the infection experiments with HTLV-III. The cell growth is indicated in number of cells, the viability (%) in number of viable cells ×100/number of total cells, and the infected cell rate (%) in number of fluorescent-positive cells x 100/number of total cells.

FIGS. 9–22 demonstrate that when no test compound was added to the medium, the cells did not grow and were killed by viral infection, whereas depending on the increase in the dose of the test substance, the number of cells and viability approached the values of the control without virus. Also, it is shown from FIGS. 23–29 that when the test substance is not added, almost all cells were infected (−100%), whereas depending on the increase in the dose of the test substances, the infection of cells was strongly inhibited.

Accordingly, it is evident that the test substances have excellent inhibiting activities against infection of AIDS virus to host cells and viral proliferation.

EXAMPLE 4

(Cytotoxicity)

As the anti-virus substances often show toxicity to the host cells, the following experiment was conducted to determine whether or not the test substances (used in Example 1 ) would induce cytotoxicity.

MT-4 cells were cultured without using virus in the same manner as in Example 3 and the proliferation and viability of cells were recorded. The results are shown in the following Table.

| Substance ($\mu$g/ml) | Cell number ($\times 10^4$ cells/ml) | Viability (%) |
|---|---|---|
| Sodium dextran sulfate (molecular weight: 5000, S-content: 13%) | | |
| 100 | 121 | 93 |
| 10 | 127 | 92 |
| 1 | 123 | 90 |
| 0 | 124 | 87 |
| Sodium dextran sulfate (molecular weight: 7000–8000, S-content: 17–20%) | | |
| 100 | 130 | 94 |
| 10 | 138 | 91 |
| 1 | 120 | 90 |
| 0 | 124 | 87 |
| Sodium dextran sulfate (molecular weight: 500,000 S-content: 16%) | | |
| 100 | 126 | 86 |
| 10 | 139 | 94 |
| 1 | 124 | 88 |

-continued

| Substance (μg/ml) | Cell number (×10⁴ cells/ml) | Viability (%) |
| --- | --- | --- |
| 0 | 124 | 87 |
| Fucoidin | | |
| 100 | 71 | 93 |
| 10 | 112 | 99 |
| 1 | 141 | 92 |
| 0 | 124 | 87 |
| κ-Carrageenan 80% + λ-Carragheenan 20% | | |
| 100 | 111 | 92 |
| 10 | 149 | 93 |
| 1 | 147 | 93 |
| 0 | 124 | 87 |
| λ-Carrageenan | | |
| 100 | 83 | 94 |
| 10 | 203 | 94 |
| 1 | 147 | 89 |
| 0 | 124 | 87 |
| ι-Carrageenan | | |
| 100 | 144 | 80 |
| 10 | 128 | 93 |
| 1 | 135 | 94 |
| 0 | 124 | 87 |

The above results show that the test substances have little cytotoxicity.

EXAMPLE 5

Inhibition of reverse transcriptase activity)

The effects of the test substances on the reverse transcriptase activity of AMV were evaluated by the method described in Example 1. The test substances used are chondroitin sulfate (S-content: 6.2–6.9%), chondroitin polysulfate (S-content: 11.6–12.1%), keratin sulfate (S-content: content: 7.0–8.0%), and keratan polysulfate (S-content: 9.7%). The results are shown in FIGS. 30–33.

FIGS. 30–33 indicate that the enzyme inhibition increases with the increasing doses of the above test substances. The above results also demonstrate that the reverse transcriptase inhibitory activity of the test substances is closely related to the number of sulfate group in the molecule, as evidenced by the fact that the synthetic substances (e.g. condroitin polysulfate and keratan polysulfate) have stronger activity than the natural substances (e.g. condroitin sulfate and keratan polysulfate).

EXAMPLE 6

(Anti-AIDS virus activity)

Test substances were assayed for the anti-AIDS virus activity in the same manner as in Example 3 using cell culture. The test substances were the same as those used in Example 5. The results are shown in FIGS. 34–45, wherein ∇, Δ and □ show the controls without virus ▼, ▲ and ■ show the infection tests with virus.

FIGS. 34–41 demonstrate that, without the test substances, the cells did not grow and were killed by viral infection, whereas depending on the increase in the dose of the test substance, the decrease in number of cells and loss of viability were prevented. Also, FIGS. 42–45 demonstrate that when the test substance was not present, almost all of the cells were infected (−100%) with HTLV-III, whereas depending on the increase in the dose of the test substances, the infected cell rate (%) was significantly reduced.

The above results also indicate that the synthetic mucopolysaccharide polysulfates having a higher S-content had stronger anti-AIDS virus activities than those of the natural products.

EXAMPLE 7

(Anti-AIDS virus activity)

The anti-AIDS virus activity of heparin was evaluated in the same manner as in Example 3. The results are shown in FIGS. 46–48, wherein ∇, Δ and □ show the controls without virus, and ▼, ▲, and ■ show the infection tests with virus.

FIGS. 46 and 47 show that without heparin, the cells did not grow and were killed by viral infection, whereas depending on the increase in the dose of heparin, the number of cells and viability were maintained to that of control. It was also shown from FIG. 48 that when heparin was not present, almost all of the cells are infected, whereas depending on the increase in the dose of heparin, they become less susceptible to the viral infection.

EXAMPLE 8

(Cytotoxicity)

As the anti-virus substances often show toxicity to the host cells, an experiment was conducted to determine whether or not heparin would induce such cytotoxicity.

Without the virus, MT-4 cells were cultured in the same manner as in Example 7, and proliferation and viability of cells were recorded. The results are shown in the following Table.

| Heparin (μg/ml) | Cell number (×10⁴ cells/ml) | Viability (%) |
| --- | --- | --- |
| 100 | 133 | 94 |
| 10 | 142 | 89 |
| 1 | 143 | 91 |
| 0 | 124 | 87 |

The above results demonstrate that heparin has little cytotoxicity.

EXAMPLE 9

(Anti-AIDS activity)

In order to examine the correlation between the anti-AIDS virus activity and the molecular structure (especially, molecular weight and S-content or number of sulfate group in this case) of various test substances including those used in Examples 1–7, the anti-AIDS activities were evaluated for the various naturally occurring polysaccharides, polysaccharides having a sulfate group, mucopolysaccharides, mucopolysaccharide sulfate, and mucopolysaccharide polysulfate. Further, similar experiments were carried out with various other sulfates which were synthetically obtained. The experimental procedures employed are identical to that in the preceding experiments. The cultured MT-4 cells were infected with HTLV-III and the inhibitory effects of various test substances on the infected cell rate (number of fluorescent cell × 100/ total cell, %) were determined at the 6th day. The results are shown in the following Table.

1) Dextrans, their synthetic sulfates, and monosaccharides having sulfate groups.

| Test substance | Molecular weight | S-content (%) | Infected cell (%)* | | |
|---|---|---|---|---|---|
| | | | 10 μg/ml | 100 μg/ml | 1000 μg/ml |
| Dextran | 9,000 | 0 | 100 | 100 | |
| " | 300,000 | 0 | 100 | 100 | |
| Dextran sulfate | 5,000 | 13 | 18 | 0 | |
| " | 8,000 | 14 | 25 | 0 | |
| " | 500,000 | 16 | 20 | 0 | |
| " | 7,000–8,000 | 17–20 | 1 | 0 | |
| " | 3,500 | 3–6 | 100 | 82 | 1 |
| (Monosaccharides) | | | | | |
| Glucose-6-sulfate | | 12 | 100 | 100 | 100 |
| Glucose-polysulfate | | 22 | 100 | 100 | 100 |
| N-acetylglucosamine polysulfate | | 18 | 100 | 100 | 100 |

*The control without test substance shows the value of 100% as the infected cell rate under the same conditions.

2) Polysaccharides derived from algae and their sulfates.

| Test substance | Molecular weight | S-content (%) | Infected cell (%) | |
|---|---|---|---|---|
| | | | 10 μg/ml | 100 μg/ml |
| κ-Carrageenan | | ≈7 | 95 | 1 |
| γ-Carrageenan | | ≈16 | 3 | 1 |
| ι-Carrageenan | | ≈12 | 100 | 31 |
| Fucoidin | | ≈15 | 32 | 1 |
| Agarose | 60,000–180,000 | 2–3 | 100 | 100 |
| Alginic acid | 32,000–240,000 | 0 | 100 | 100 |
| Alginic acid sulfate | 50,000–300,000 | 14 | 7 | 4 |

3) Chitin and chitosan and their sulfates

| Test substance | Molecular weight | S-content (%) | Infected cell (%) | |
|---|---|---|---|---|
| | | | 10 μg/ml | 100 μg/ml |
| Chitin | | 0 | 100 | 100 |
| Chitin sulfate | | 9 | 100 | 81 |
| Chitosan | | 0 | 100 | 100 |
| Chitosan sulfate | | 18 | 1 | 1 |

4) Mucopolysaccharides derived from animals, and their sulfates and polysulfates

| Test substance | Molecular weight | S-content (%) | Infected cell (%) | |
|---|---|---|---|---|
| | | | 10 μg/ml | 100 μg/ml |
| Chondroitin | 25,000–30,000 | 0 | 100 | 100 |
| Chondroitin polysulfate | 5,000–8,000 | 13 | 3 | 1 |
| Chondroitin-4-sulfate | 30,000–50,000 | 6 | 100 | 100 |
| Chondroitin-4-sulfate polysulfate | | 16 | 2 | 1 |
| Dermatan sulfate | 20,000–40,000 | 6 | 100 | 80 |
| Chondroitin-6-sulfate | 30,000–50,000 | 6 | 100 | 100 |
| Chondroitin-6-sulfate polysulfate | | 15 | 2 | 1 |
| Heparin | 7,000–30,000 | 13 | 41 | 1 |
| Heparitin sulfate | 15,000 | 7 | 100 | 90 |
| Keratan sulfate | 4,000–20,000 | 7 | 100 | 80 |
| Keratan polysulfate | | 10 | 80 | 40 |
| Hyaluronic acid | 10,000–100,000 | 0 | 100 | 100 |
| Hyaluronic acid sulfate | | 8 | 100 | 70 |

5) Other polysaccharides

None of pectin, colominic acid, inulin, raffinose, and methylcellulose showed any anti-AIDS virus activities.

From the above results, it can be clearly seen that the anti-AIDS virus activity is closely related to the S-content or number of sulfate group in this case rather than to the molecular weight. Substances without a sulfate group showed no anti-AIDS activity. Further, the anti-AIDS activity was intensified with increasing S-content (number of sulfate group) of the molecule. With respect to the relation with the molecular weight, there was no effect at all in the monosaccharides. However, in the substances having molecular weights of 5,000 and higher, the increase of the molecular weight did not affect the anti-AIDS virus activity as seen in, e.g., dextran sulfate.

This is quite different from the pattern of manifestation of heretofore known activities of polysaccharide sulfates against herpes virus.

In view of the fact that the polysaccharides with higher molecular weight and their sulfate are known to have the high toxicities to human being and animals, the experimental evidence obtained in the present invention that the dextran sulfate with lower molecular weight show sufficient anti-AIDS activity, is extremely important in developing it as a medicament for prevention and therapy of the viral disease.

Among the above test substances, those which showed particularly strong anti-AIDS virus activities are dextran sulfate, λ-carrageenan, alginic acid sulfate, chitosan sulfate, chondroitin polysulfates, further sulfated chondroitin-4-sulfate and -6-sulfate, heparin, etc. having S-content more than 10%.

EXAMPLE 10

(Anti-Friend leukemia virus (F-MuLV) activity)

Procedure 1

Anti-FMuLV activity of dextran sulfate (molecular weight: 7000–8000, S-content: 17–20%) was determined by a XC-plaque assay method. BALB3T3 cells were cultured in adhesive form in a 35 mm-dish at $5 \times 10^4$ cells/dish (2 ml). After removing the culture medium, a fresh medium with or without indicated concentrations of the test substance (1 ml each) and 0.2 ml of the virus preparation were charged, and the cells were cultured overnight. On the following day, the culture media were replaced with those (2 ml) containing or not containing the above substances, the incubation was continued for three additional days to progress the infection and replication of the virus. After the removal of the medium, the further progression of viral replication was stopped by UV irradiation. To this dish, the suspension of XC-cells (2 ml) was added and cultured for three days and the plaque formation produced by the virus particle induced cell-fusion, was observed. The number of plaques was shown in the following Table.

TABLE

Anti-Freind leukemia virus activity by Procedure 1

| DS ($\mu$g/ml) | Number of plaques per dish | Inhibition (%) |
|---|---|---|
| Control | 168 | (0) |
| 1 | 14 | 92 |
| 5 | 12 | 93 |
| 10 | 11 | 93 |
| 50 | 13 | 92 |
| 100 | 6 | 96 |
| 1000 | 0 | 100 |

As observed from the above Table, DS inhibited 90% or more the formation of plaque at the concentrations of 1–100 $\mu$g/ml, indicating that the infection and replication of the virus was strongly inhibited. The plaque formation was not detected at 1,000 $\mu$g/ml of DS.

DS at 1–100 $\mu$g/ml did not show any cytotoxicity to BALB 3T3 cells.

Procedure 2

Procedure 1 was repeated except that after adsorption of the virus in the medium without DS, the non-adsorbed viruses were removed and the culture was carried out in the medium (2 ml) containing or not containing DS. The results are shown in the following table.

TABLE

Anti-Friend leukemia virus activity by Procedure 2:

| DS ($\mu$g/ml) | Number of plaques per dish | Inhibition (%) |
|---|---|---|
| Control | 35 | (0) |
| 0.01 | 33 | 6 |
| 0.1 | 19 | 45 |
| 1 | 14 | 61 |
| 10 | 17 | 52 |
| 100 | 16 | 54 |
| 500 | 0 | 100 |

The above results indicate that, also in Procedure 2, DS inhibited the infection and replication of the virus by about 60% at the concentration of 1 $\mu$g/ml, and almost completely at 500 $\mu$g/ml. From the above results, it is evidenced that DS inhibits the infection and replication of the oncogenic virus (Oncovirinae) including F-MuLV, as well as the cytolytic virus (Lentivirinae) including AIDS-virus.

EXAMPLE 11

(Inhibition of viral infection)

Procedure

1. Virus deactivating effect:

Virions from HTLV-III were added to a culture medium containing 100 ug/ml of test compounds, which was kept at 37° C. for 60 minutes. After diluting 1,000 fold, the resulting virus solution was added to MT-4 cells to initiate infection. At that time, the ratio of cells to virus was 500:1. After incubating at 37° C. under 5% $CO_2$ for 3 days, an antibody to virus antigen was reacted and the effects were compared by determining the rate of infected cells (%) by indirect fluorescent antibody technique. The rate of infected cells is expressed by the number of the fluorescent positive cells × 100/total number of cells.

2. Virus removing effect:

Virions from HTLV-III were added to a culture medium containing 10$\mu$g/ml of test compounds, which was immediately added to MT-4 cells. After incubating at 37° C. for 60 minutes, the culture was centrifuged and the supernatant was removed. Viruses which were not adsorbed to the cells were removed by washing twice with physiological phosphate buffer. Fresh culture medium was added to the washed cells and the culture was incubated at 37° C. under 5% $CO_2$ for 3 days. On the third day, the effects were compared by determining the rate of infected cells (%) by indirect fluorescent antibody technique.

3. Inter-cellular propagation inhibiting effect:

HTLV-III/Molt 4 cells, cells infected with HTLV-III and producing AIDS virus, were mixed with Molt-4 cells not infected with AIDS virus in a ratio of 1:9, and they were incubated at 37° C. under 5% $CO_2$ for 4 days. The mixture was prepared so that the culture contained 10 $\mu$g/ml of test substance. On the fourth day, the effects were compared by determining the rate of infected cells (%) by an indirect fluorescent antibody technique.

Results

| compound | M.W. | S-content* | Rate of infected cells (%) | | |
|---|---|---|---|---|---|
| | | | Process 1 | Process 2 | Process 3 |
| Non (uninfected control) | — | — | 0 | 0 | (10)** |
| Non (infected control) | — | — | 100 | 100 | 100 |
| $\lambda$-carrageenan | — | ≈16 | 30 | <5 | 10 |
| alginic acid sulfate | 50,000~300,000 | ≈14 | 30 | <5 | 10 |
| chitosan sulfate | — | 18 | 30 | <5 | 10 |
| dextran sulfate | 500,000 | 16 | 30 | <5 | 10 |
| dextran sulfate | 7,000~8,000 | 17~20 | 40 | <5 | <5 |
| chondroitin polysulfate | 5,000~8,000 | 13 | 40 | <5 | <5 |

*S-content is originated from sulfate and sulfonate groups attached to the saccharic chain.
**Rate of infected cells = fluorescent positive cells × 100/total cells From the above results, it can be clearly seen that the test compounds, dextran sulfate and other similar sulfated polysaccharides strongly inhibited the process of adsorption of HIV virion to the receptor of a target cell, i.e. the first step of the establishment of viral infection.

Consequently, it can be inferred that the cell fusion inhibiting activity of dextran sulfate and other similar sulfated polysaccharide results from an inhibiting activity against the adsorption of HIV antigen presumably generated on the surface of the infected cell to the receptor of the uninfected cell.

What is claimed is:

1. A method of topically cleansing at least a portion of the human body that may have been brought into contact with body fluid containing human retrovirus which comprises cleansing said portion of the human body with a topical cleansing agent consisting essentially of a cleansing vehicle containing from 2.5 to 2,000 ppm of a compound having saccharic carbon atoms, said compound being dextran sulfate having a molecular weight of from 2,000 to 10,000 wherein said compound has at least 5% sulfur content provided by s-oxoacid groups attached to said saccharic carbon atoms through a linking group of about 14 to about 32 molecular weight.

2. The method according to claim 1, wherein said S-oxoacid groups are sulfo groups (—SO$_3$H).

3. The method according to claim 1, wherein said linking group is selected from the group consisting of an oxo group (—O—) and an imino group (—NH—).

4. The method according to claim 1, wherein said retrovirus is a human immunodeficiency retrovirus.

5. The method according to claim 4, wherein said human retrovirus is selected from human T-lymphotropic virus-III, lymphadenopathy associated virus-1, lymphadenopathy associated virus-2, AIDS-related virus and human T-lymphotropic virus-IV.

6. The method according to claim 4, wherein said human retrovirus is human T-lymphotropic virus-I, human T-lymphotropic virus-II or a causative virus for Kawasaki disease.

7. The method according to claim 1, wherein said dextran sulfate has inhibitory activity against reverse transcriptase of the human retrovirus.

8. The method according to claim 1, wherein said dextran sulfate is a sulfuric acid ester of dextran.

9. The method according to claim 8, wherein said dextran sulfate has at least one hydrogen sulfate group (—O—SO$_3$H).

10. A method of topically cleansing at least a portion of the human body that may have been brought into contact with body fluid containing human retrovirus which comprises cleansing said portion of the human body with a topical cleansing agent composition consisting essentially of a compound having saccharic carbon atoms, said compound being dextran sulfate having a molecular weight of from 2,000 to 10,000, wherein said compound has at least 5% sulfur content provided by s-oxoacid groups attached to said saccharic carbon atoms through a linking group of about 14 to about 32 molecular weight and wherein said cleansing agent provide a concentration of 2.5 to 2,000 ppm of said compound on said human.

11. The method according to claim 10, wherein said S-oxoacid groups are sulfo groups (—SO$_3$H).

12. The method according to claim 10, wherein said linking group is selected from the group consisting of an oxo group (—O—) and an imino group (—NH—).

13. The method according to claim 10, wherein said retrovirus is a human immunodeficiency retrovirus.

14. The method according to claim 13, wherein said human retrovirus is selected from human T-lymphotropic virus-III, lymphadenopathy associated virus-1, lymphadenopathy associated virus-2, AIDS-related virus and human T-lymphotropic virus-IV.

15. The method according to claim 13, wherein said human retrovirus is human T-lymphotropic virus-I, human T-lymphotropic virus-II or a causative virus for Kawasaki disease.

16. The method according to claim 10, wherein said dextran sulfate has inhibitory activity against reverse transcriptase of the human retrovirus.

17. The method according to claim 10, wherein said dextran sulfate is a sulfuric acid ester of dextran.

18. The method according to claim 17, wherein said dextran sulfate has at least one hydrogen sulfate group (—O—SO$_3$H).

* * * * *